United States Patent
Gaiser et al.

(10) Patent No.: US 7,077,841 B2
(45) Date of Patent: Jul. 18, 2006

(54) SYSTEMS AND METHODS EMPLOYING A GUIDEWIRE FOR POSITIONING AND STABILIZING EXTERNAL INSTRUMENTS DEPLOYED WITHIN THE BODY

(75) Inventors: John Gaiser, Mountain View, CA (US); Scott West, Livermore, CA (US); David S Utley, Redwood, CA (US); David Huynh, Santa Clara, CA (US)

(73) Assignee: Curon Medical, Inc., Fremont, CA (US)

( * ) Notice: Subject to any disclaimer, the term of this patent is extended or adjusted under 35 U.S.C. 154(b) by 375 days.

(21) Appl. No.: 10/017,906

(22) Filed: Dec. 14, 2001

(65) Prior Publication Data

US 2002/0151871 A1    Oct. 17, 2002

Related U.S. Application Data

(60) Provisional application No. 60/278,738, filed on Mar. 26, 2001.

(51) Int. Cl.
*A61B 18/18*    (2006.01)

(52) U.S. Cl. .................. 606/41; 606/191; 606/200; 604/523

(58) Field of Classification Search ............. 604/96.01, 604/103.04, 523, 528, 264; 606/32, 41, 200, 606/34, 191; 600/434–435
See application file for complete search history.

(56) References Cited

U.S. PATENT DOCUMENTS

| | | | |
|---|---|---|---|
| 5,100,423 A * | 3/1992 | Fearnot .................... 606/159 |
| 5,305,742 A | 4/1994 | Styers et al. |
| 5,344,413 A * | 9/1994 | Allman et al. .............. 604/523 |
| 5,383,853 A * | 1/1995 | Jung et al. ............. 604/103.04 |
| 5,395,332 A * | 3/1995 | Ressemann et al. ...... 604/103.1 |
| 5,443,457 A * | 8/1995 | Ginn et al. ................ 604/528 |
| 5,456,667 A * | 10/1995 | Ham et al. ................... 604/107 |
| 5,549,553 A * | 8/1996 | Ressemann et al. ... 604/103.08 |
| 5,549,556 A * | 8/1996 | Ndondo-Lay et al. ... 604/103.1 |
| 5,571,087 A * | 11/1996 | Ressemann et al. ...... 604/96.01 |
| 5,626,128 A | 5/1997 | Bradley et al. |
| 5,730,698 A * | 3/1998 | Fischell et al. ................ 600/3 |
| 5,752,932 A * | 5/1998 | Ellis et al. ............... 604/96.01 |
| 5,797,948 A * | 8/1998 | Dunham ..................... 606/194 |
| 5,830,227 A * | 11/1998 | Fischell et al. ............. 606/194 |
| 5,894,840 A | 4/1999 | King |
| 5,921,958 A * | 7/1999 | Ressemann et al. ...... 604/96.01 |
| 6,006,755 A | 12/1999 | Edwards |
| 6,036,689 A | 3/2000 | Tu et al. |
| 6,044,846 A | 4/2000 | Edwards |
| 6,056,744 A | 5/2000 | Edwards |
| 6,092,528 A | 7/2000 | Edwards |
| 6,254,598 B1 * | 7/2001 | Edwards et al. .............. 606/41 |
| 6,464,689 B1 | 10/2002 | Qin et al. |
| 6,464,697 B1 | 10/2002 | Edwards et al. |

(Continued)

FOREIGN PATENT DOCUMENTS

WO    WO 96/10434    *    4/1996

(Continued)

*Primary Examiner*—LoAn H. Thanh
(74) *Attorney, Agent, or Firm*—Ryan Kromholz & Manion, S.C.

(57) ABSTRACT

Systems and methods for treating a tissue region employ an expandable structure projecting beyond the distal end of a catheter tube. A distal tail projects beyond the far end of the basket assembly. The distal tail includes a guidewire lumen that accommodates passage of a guidewire without threading the guidewire through the catheter tube.

8 Claims, 42 Drawing Sheets

U.S. PATENT DOCUMENTS

| | | |
|---|---|---|
| 6,544,226 B1 | 4/2003 | Gaiser et al. |
| 6,547,776 B1 | 4/2003 | Gaiser et al. |
| 6,589,238 B1 | 7/2003 | Edwards et al. |
| 6,645,201 B1 | 11/2003 | Utley et al. |
| 6,699,243 B1 | 3/2004 | West et al. |
| 6,733,495 B1 | 5/2004 | Bek et al. |
| 6,783,523 B1 | 8/2004 | Qin et al. |
| 6,827,713 B1 | 12/2004 | Bek et al. |

FOREIGN PATENT DOCUMENTS

| | | |
|---|---|---|
| WO | WO 2004/112629 | 12/2004 |

* cited by examiner

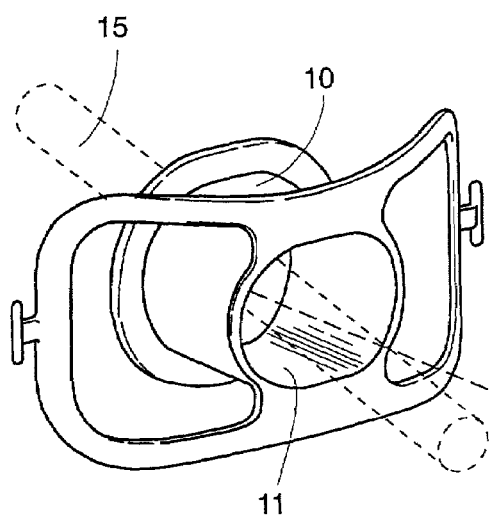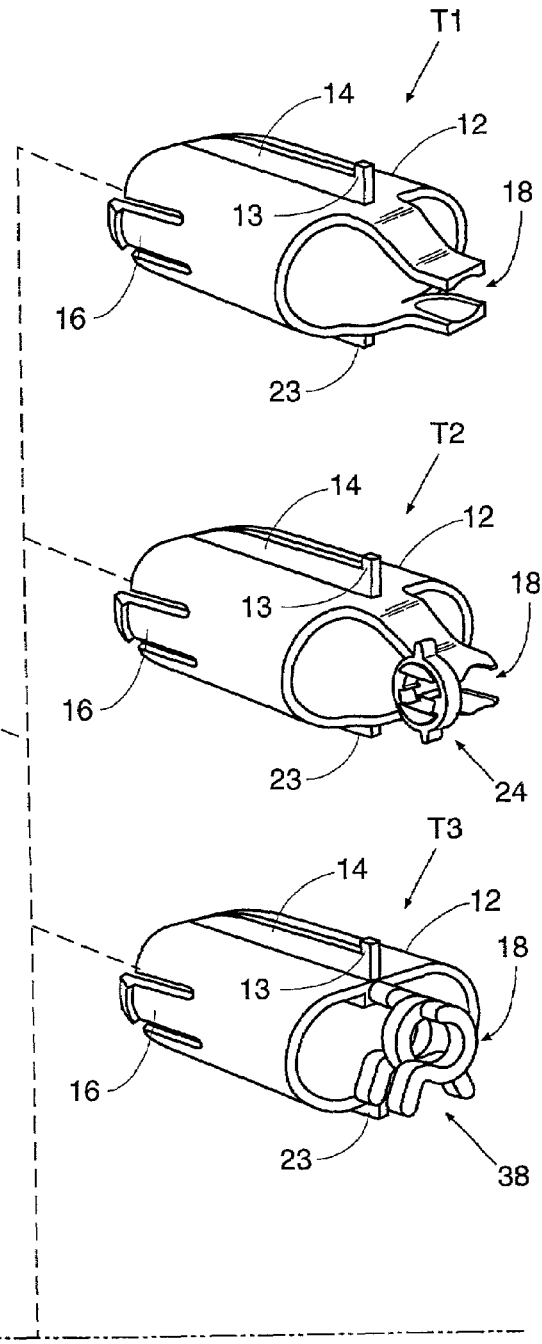
Fig. 1a-a
| Fig. 1a-a |
| Fig. 1a-b |

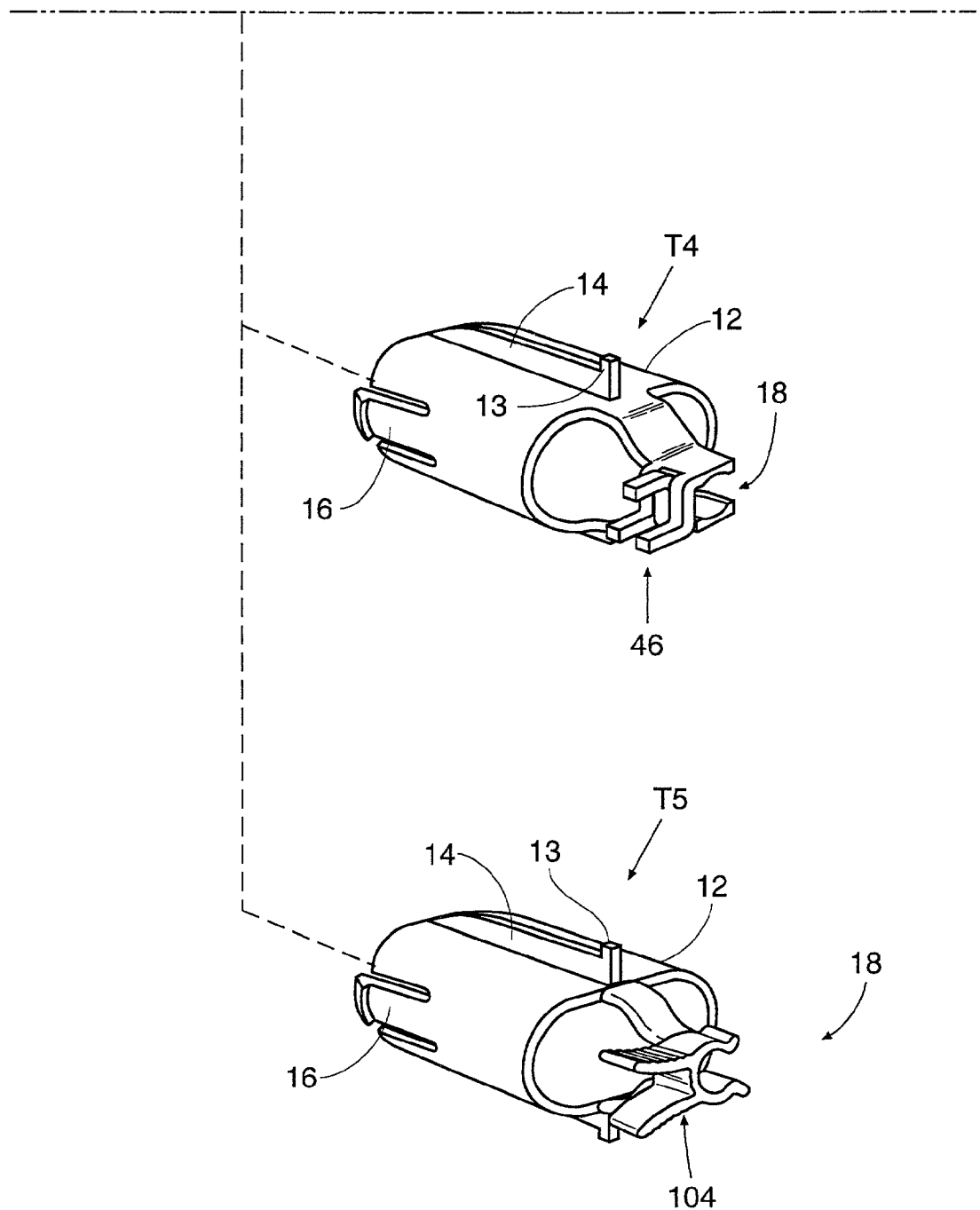
Fig. 1a-b

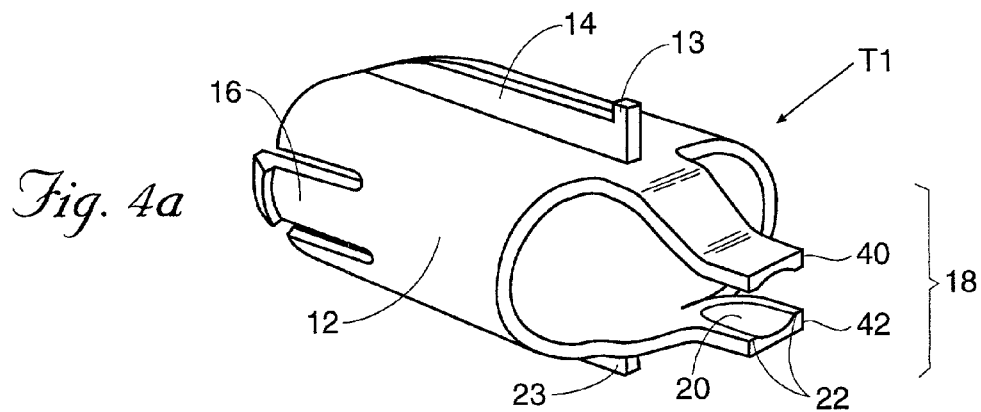
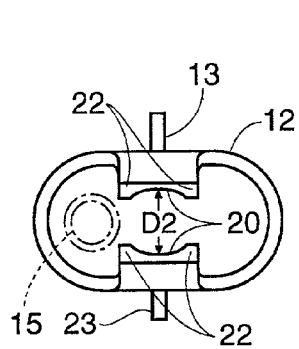 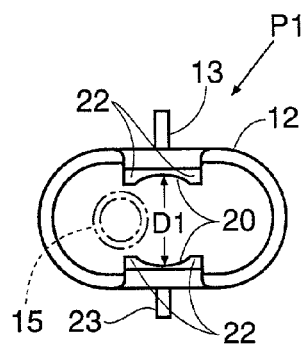 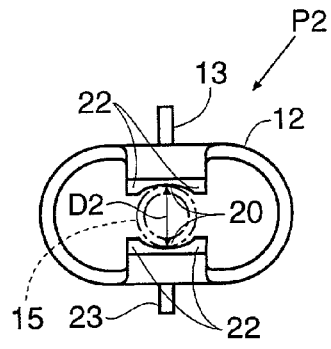
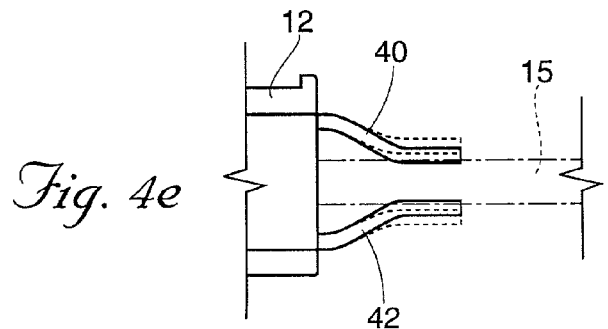

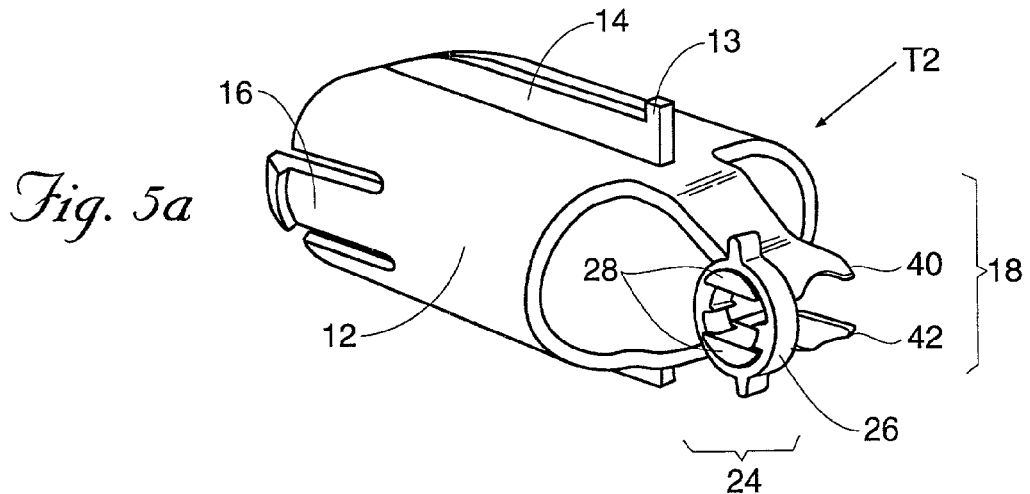
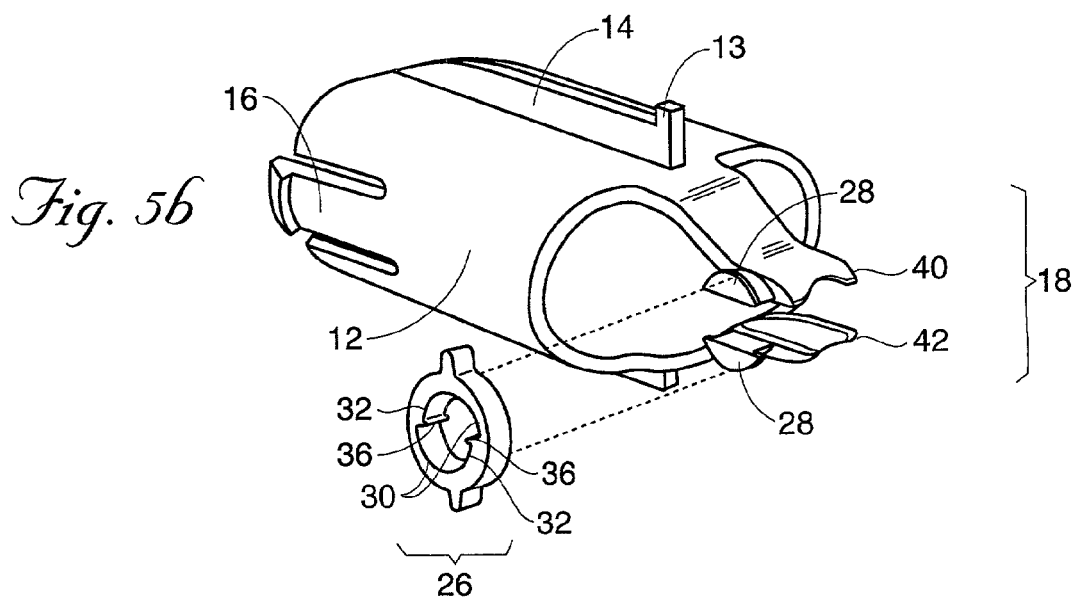
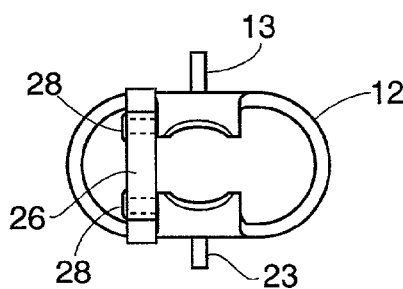

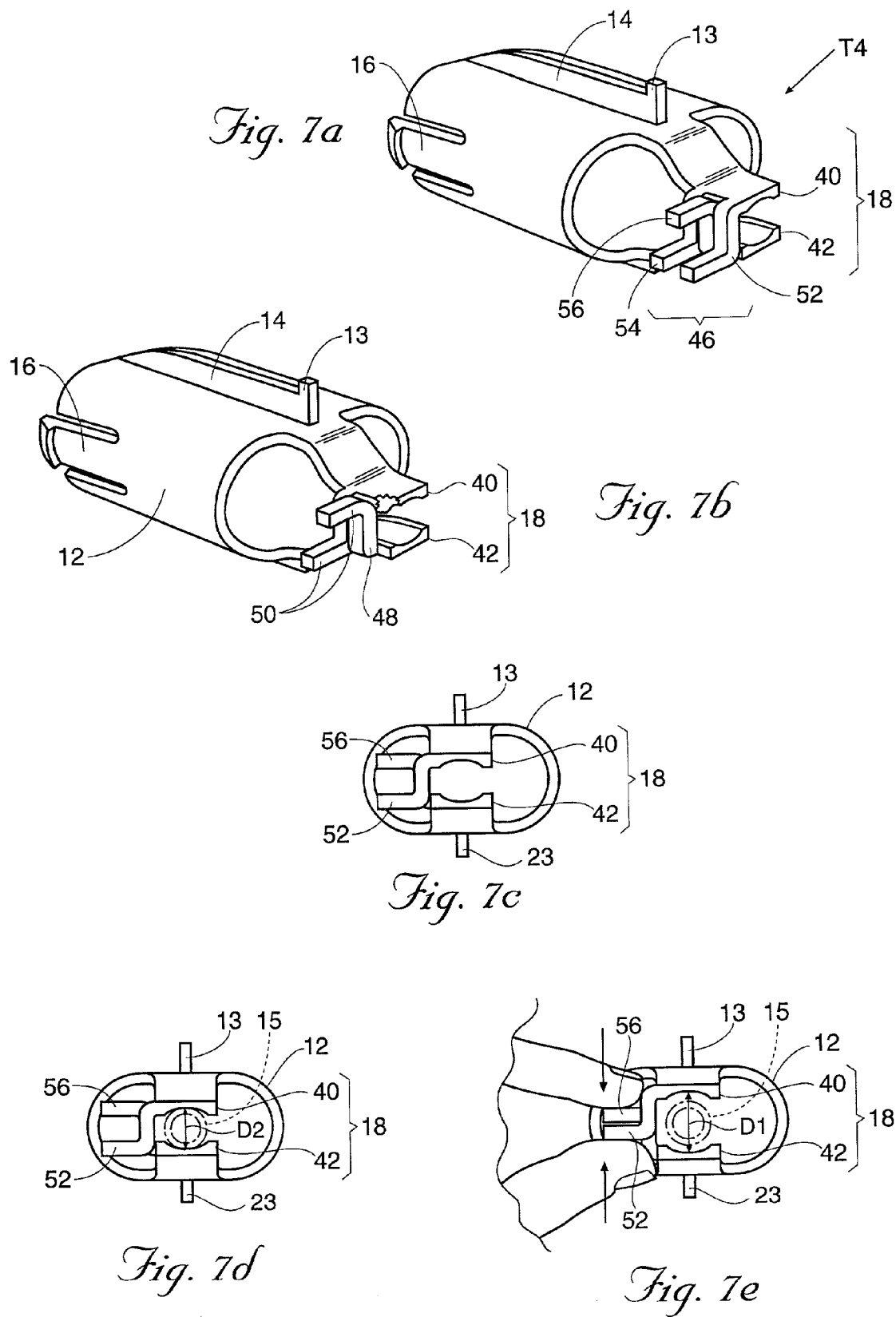

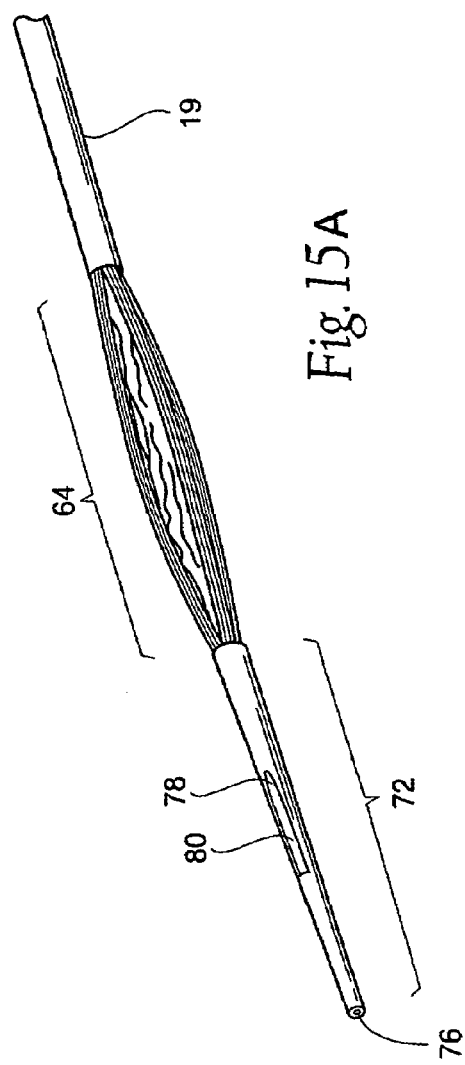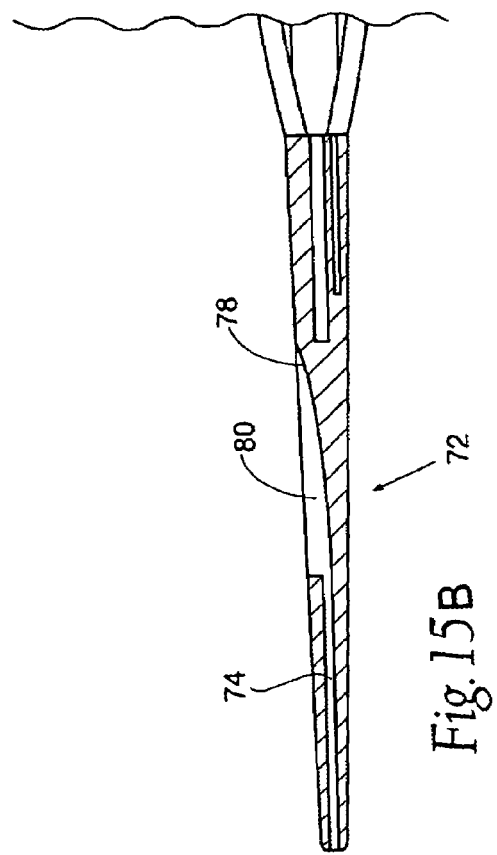
Fig. 15A
Fig. 15B

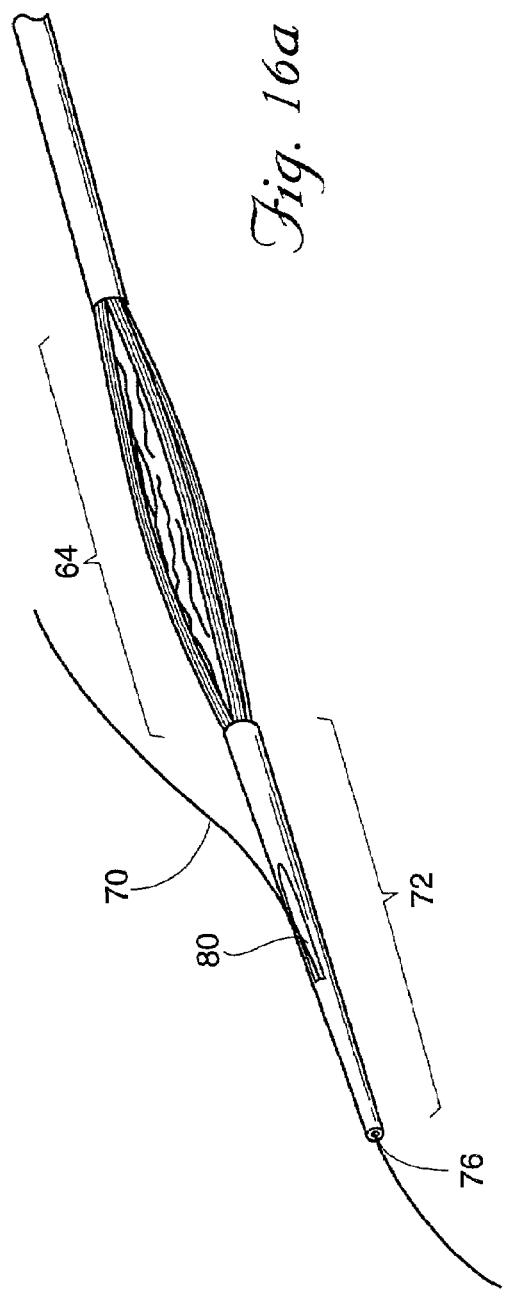
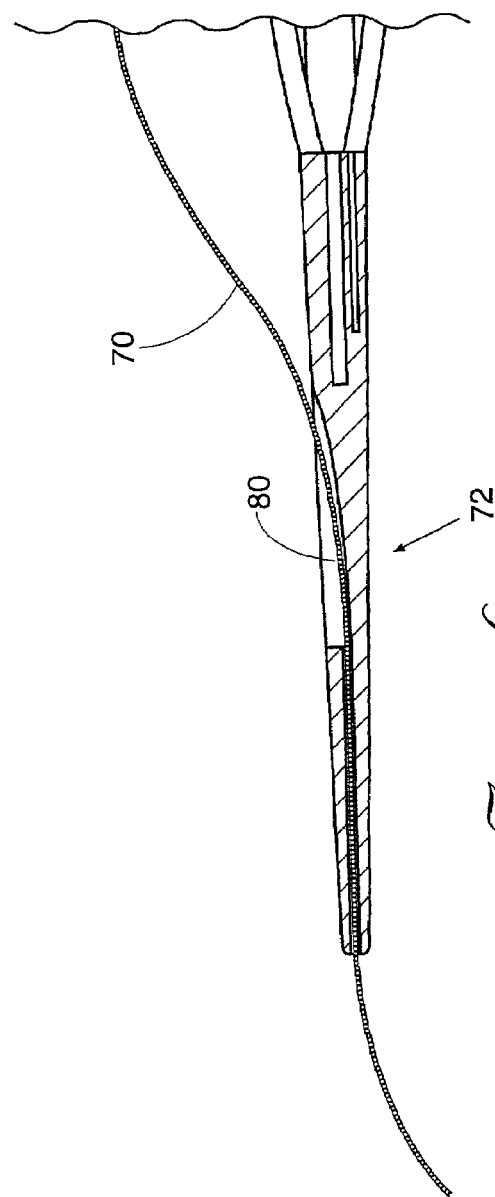

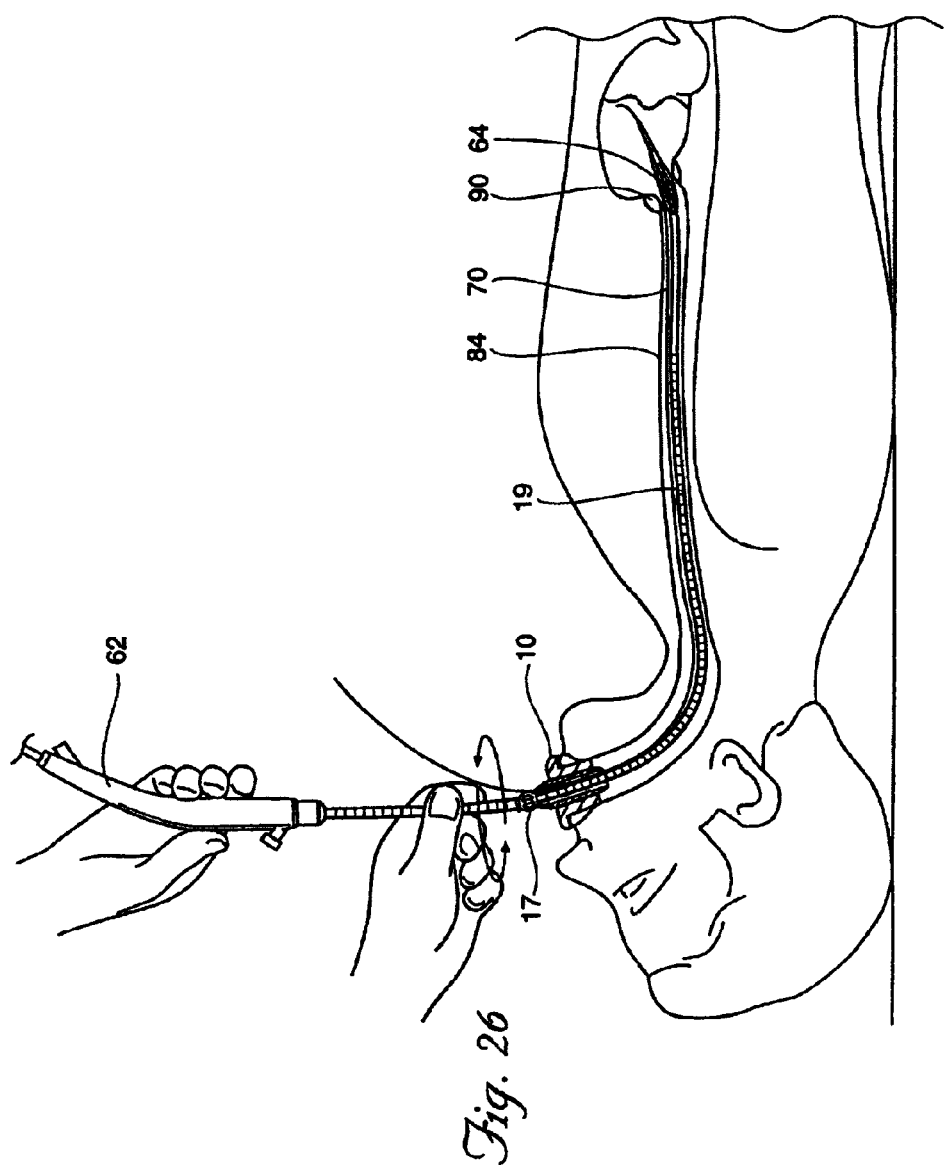

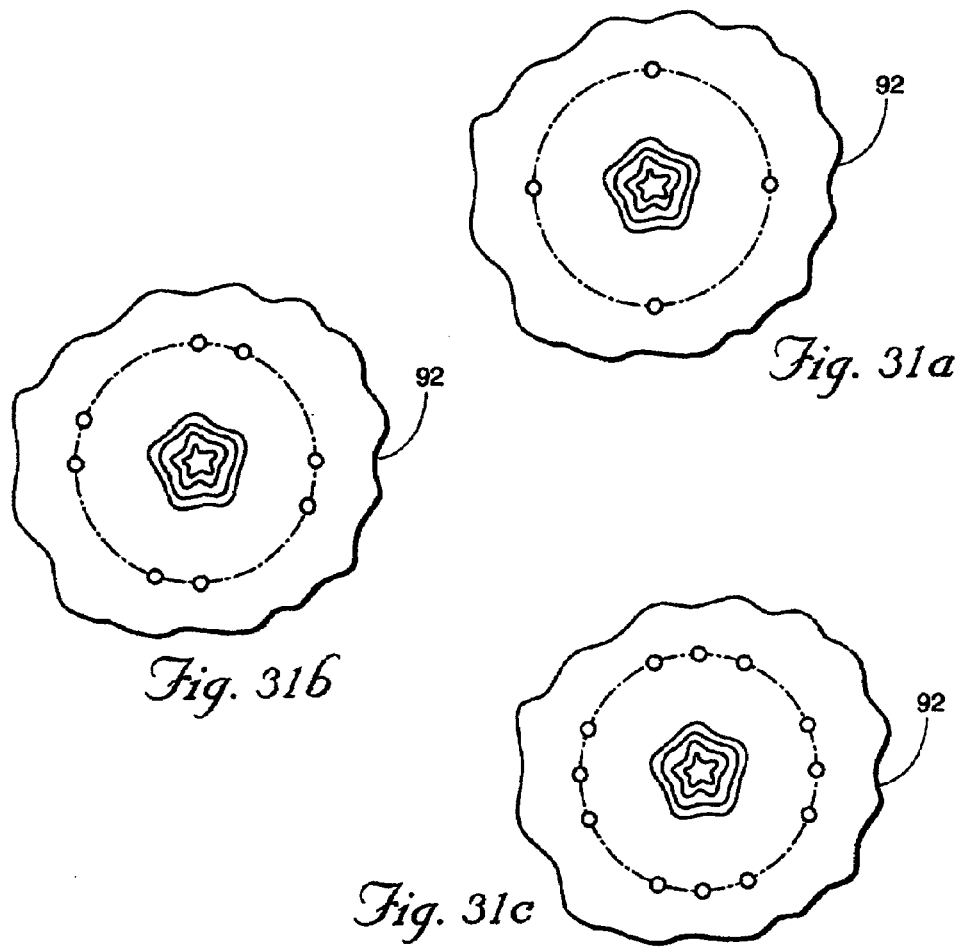
Fig. 31a
Fig. 31b
Fig. 31c
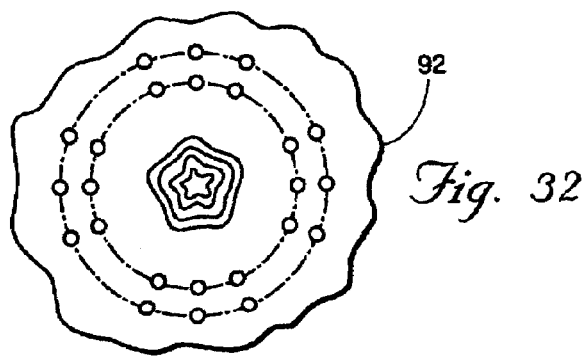
Fig. 32

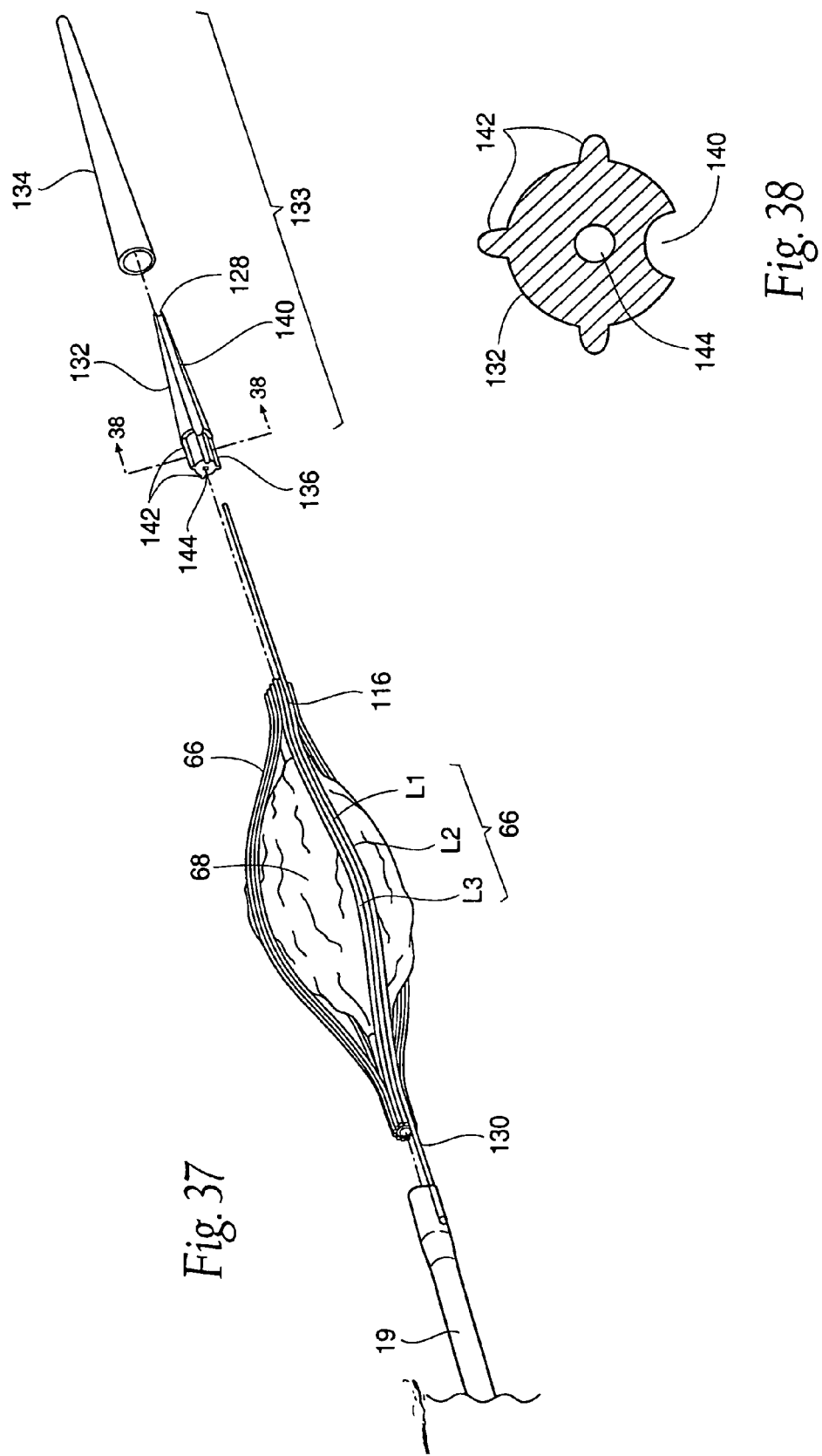

SYSTEMS AND METHODS EMPLOYING A GUIDEWIRE FOR POSITIONING AND STABILIZING EXTERNAL INSTRUMENTS DEPLOYED WITHIN THE BODY

RELATED APPLICATION

This application claims the benefit of the filing date of copending provisional U.S. Patent Application Ser. No. 60/278,738, filed Mar. 26, 2001, and entitled "Systems and Methods for Positioning and Stabilizing External Instruments Deployed within the Body."

FIELD OF THE INVENTION

The invention generally relates to systems and methods for inserting and securing the position of an external instrument, such as a catheter tube, in the body, e.g., through the oral cavity and into the esophagus for the treatment of gastric esophageal reflux disease (GERD).

BACKGROUND OF THE INVENTION

Procedures requiring insertion of an external instrument into the body, e.g., through the oral cavity into the esophagus, are known. Bite blocks are typically used to hole the patient's mouth open during these procedures. During these procedures, it also may be necessary to locate the instrument in an intended position. It may also be necessary to stabilize the instrument in an intended position.

There remains a need for simple, cost-effective ways to introduce an instrument through the oral cavity to locate the instrument and to selectively maintain the instrument in a fixed and stable position during a given medical procedure.

SUMMARY OF THE INVENTION

The invention provides systems and methods for treating a tissue region. The systems and methods employ an expandable structure that projects beyond the distal end of a catheter tube. A distal tail projects beyond the far end of the basket assembly. The distal tail includes a guidewire lumen that accommodates passage of a guidewire without threading the guidewire through the catheter tube.

BRIEF DESCRIPTION OF THE DRAWINGS

FIGS. 1*a*-*a*/1*a*-*b* is a side view of a bite block and five alternate embodiments of inserts carrying a centrally located gripping tool that may be employed with the bite block.

FIG. 4*a* is a side view of one of the embodiments shown in FIG. 1*a*-*a*.

FIGS. 4*b*–4*d* are front views illustrating the operation of the cam surfaces incorporated in the jaws of the insert shown in FIG. 4*a*.

FIG. 4*e* is a side view illustrating the open and closed positions of the jaws of the gripping tool shown in FIG. 4*a*.

FIG. 5*a* is a side view of an embodiment shown in FIG. 1*a*-*a* that incorporates a cam mechanism.

FIG. 5*b* is an exploded view of FIG. 5*a*.

FIG. 5*c* is a front view of the insert shown in FIG. 5*a*.

FIG. 7*a* is a side view of an embodiment shown in FIG. 1*a*-*b* that incorporates a prong-clamp mechanism.

FIG. 7*b* is a breakaway view of FIG. 7*a*.

FIG. 7*c* is a front view of the insert shown in FIG. 7*a*.

FIG. 7*d* is a front view of the insert shown in FIG. 7*a*, illustrating the position of the jaws of the gripping tool in the closed position.

FIG. 7*e* is a front view of the insert shown in FIG. 7*a*, illustrating the use of the prong clamp and the position of the jaws of the gripping tool in the open position.

FIGS. 8*d*-8*f* are front views illustrating the insertion of an external instrument into a bite block utilizing the upturned edges incorporated in the jaws of the insert shown in FIG. 8*a*.

FIG. 10b is a rear view of the insert shown in FIG. 10a.

FIG. 10c is a front view of a bite block incorporating the insert shown in FIG. 10a.

FIG. 11b is a rear view of the insert shown in FIG. 11a.

FIG. 11c is a front view of a bite block incorporating the insert shown in FIG. 11a.

FIG. 15a is an enlarged side view of the distal tail of the expandable structure shown in FIGS. 14a and 14b.

FIG. 15b is a cutaway side view of the distal tail shown in FIG. 15a, detailing the interior lumen within the tail.

FIG. 16a is a side view of a guidewire being threaded through the distal tail.

FIG. 16b is a cutaway view of the distal tail illustrating the threading of a guidewire through the interior lumen within the tail.

FIG. 26 is a side view of the employed catheter being rotated axially, with the expandable structure deflated and the electrodes retracted.

FIG. 31a is a schematic of a lesion pattern after one ablation sequence.

FIG. 31b is a schematic of a lesion pattern after a second ablation sequence is performed following a 22.5° rotation of the catheter.

FIG. 31c is a schematic of a lesion pattern after a third ablation sequence is performed following a 22° rotation of the catheter in the opposite direction.

FIG. 32 is a schematic of a lesion pattern after three ablation sequences separated by 22.5° are performed at each of two levels.

FIG. 36b illustrates the interior surface of the spine shown in FIG. 36a.

FIG. 37 is an exploded view of the expandable structure carried at the distal region of the catheter shown in FIG. 33, illustrating the guidewire lumen carried by a spine and a two-piece distal guide assembly.

FIG. 38 is a cross-section view of the inner sheath taken generally along line 38—38 in FIG. 37.

DESCRIPTION OF THE PREFERRED EMBODIMENT

I. The Bite Block

Figure 1B:
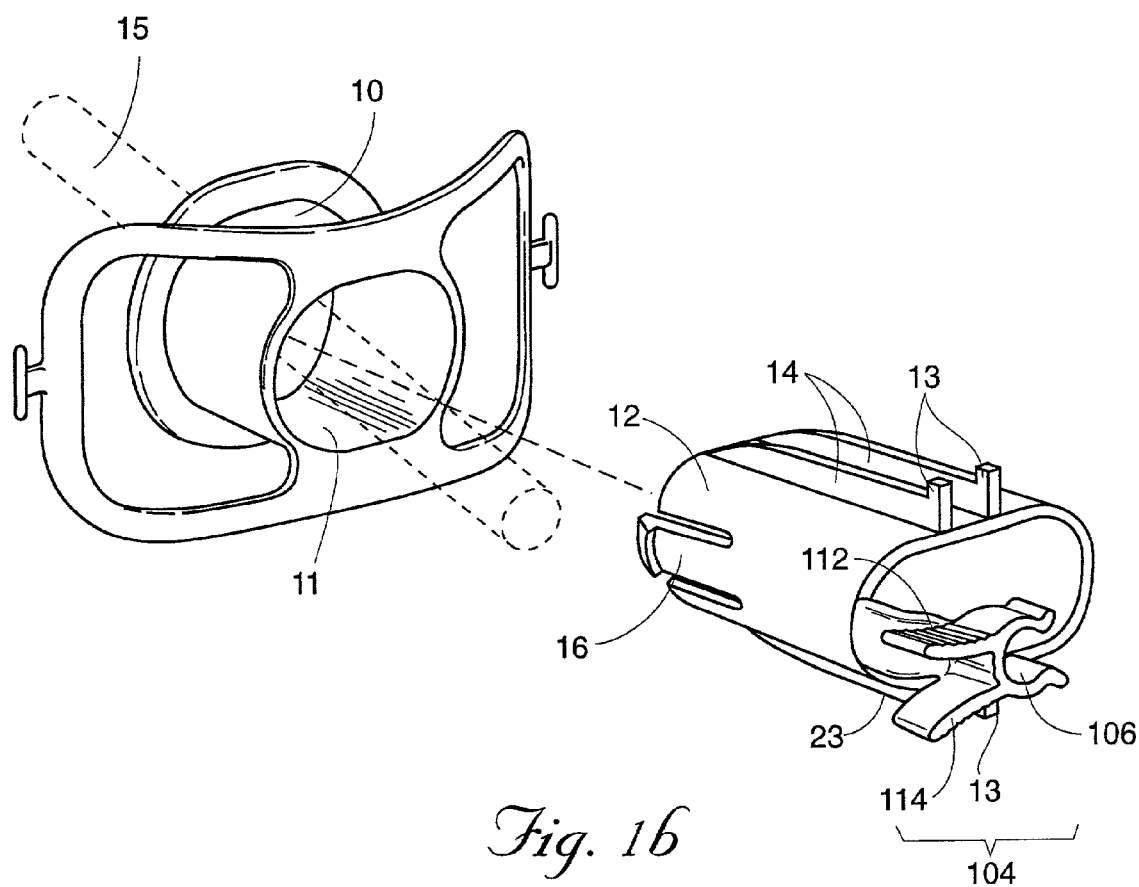
FIG. 1*b* is a side view of a bite block and an embodiment of an insert carrying an eccentrically located gripping tool that may be employed with the bite block.

FIGS. 1a-a/1a-b shows a bite block 10. A bite block 10 is commonly used to hold an individual's mouth open during insertion of an instrument into the oral cavity. For example (see FIG. 21a), a bite block 10 can be utilized during procedures requiring insertion of a catheter tube 19 through the oral cavity into the esophagus 84, such as in the treatment of gastroesophageal reflux disease (GERD).

The bite block 10 may be conventional, formed, e.g., from hard, medical grade plastic by conventional molding techniques.

Conventional bite blocks 10 comprise an opening 11 for insertion of an external instrument 15 (as shown in phantom lines in FIG. 1a). Typically, the opening 11 is large enough to readily accommodate insertion of a variety of differently sized and shaped instruments and is therefore not capable of holding an instrument in a fixed or stabilized position.

As a result, insertion of an instrument 15 through the bite block 10 does not automatically result in the instrument 15 being held in the proper position. Correct positioning of the instrument 15 is generally useful to effective performance of a procedure.

It is therefore necessary for an individual performing a procedure (or an assistant) to hold the instrument 15 in the proper position, often for extended periods of time. This can be both cumbersome and difficult to do.

Figure 1C:
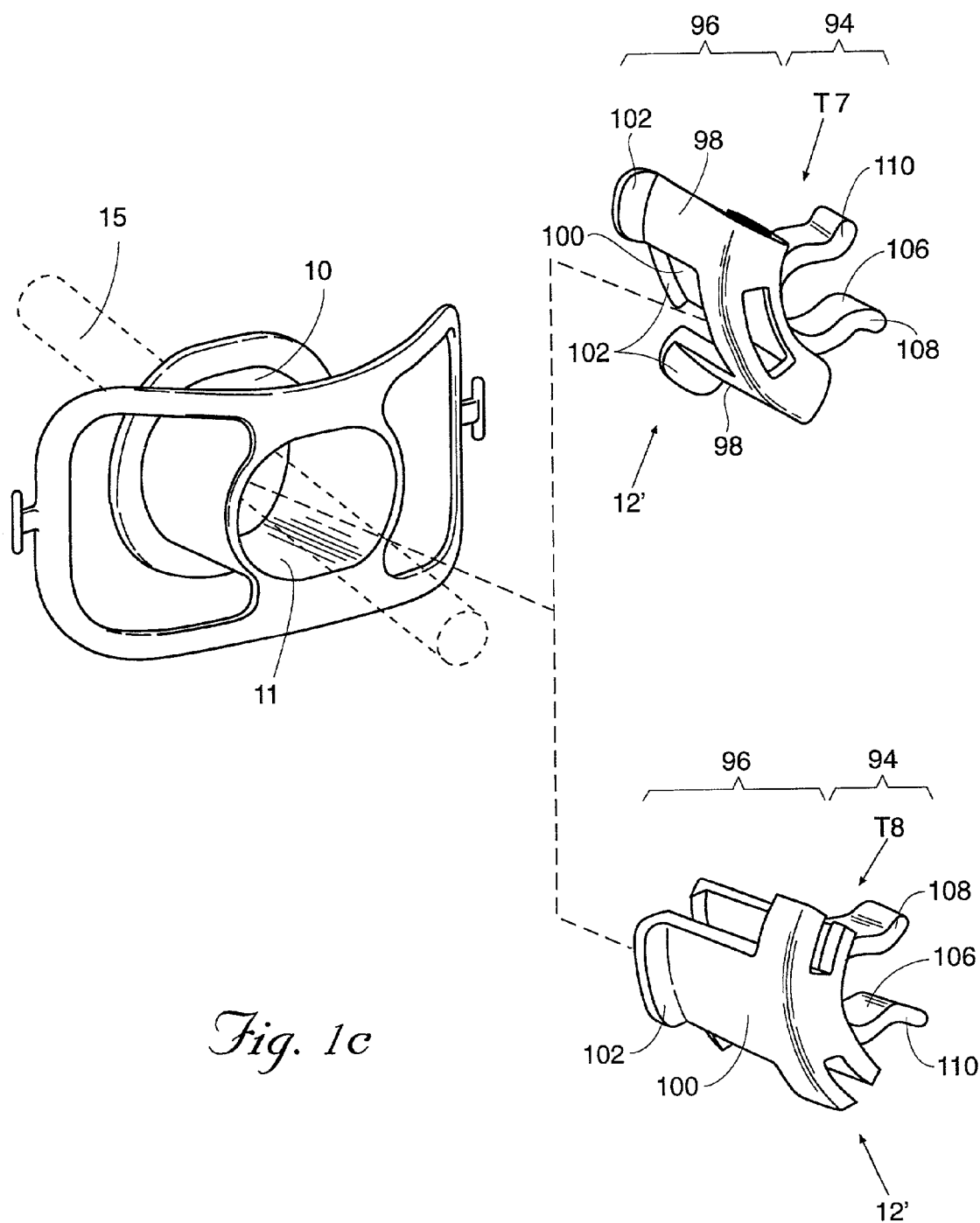
FIG. 1*c* is a side view of a bite block and two alternate embodiments of "clip-on" inserts carrying eccentrically located gripping tools that may be employed with the bite block.

One aspect of the invention provides for a gripping tool (T) for association with a bite block 10. Eight embodiments of a gripping tool (T1–T8) are shown in FIGS. 1a-a/1a-b, 1b, and 1c. Five of the embodiments (T1–T5) are shown in FIG. 1a-a/1a-b. Another embodiment (T6) is shown in FIG. 1b. Two additional embodiments (T7 and T8) are shown in FIG. 1c.

The gripping tool (T) holds an instrument 15 in a fixed or stabilized position within the oral cavity during a procedure and permits removal of the instrument upon completion of the procedure, as will be described in greater detail later. It further permits the moving of the instrument 15 from one fixed position to an alternate fixed position, as will also be described in greater detail later.

Thus, the invention permits the hands of the provider to be freed during the procedure and assures that the instrument 15 will not inadvertently be moved during the procedure.

The gripping tool (T) or any portion of it may be integral with the body of the bite block 10. Alternately, the gripping tool (T) or any portion of it may be part of an insert 12 that is selectively attachable within the opening 11 of the bite block 10 at the instant of use.

Figure 2:
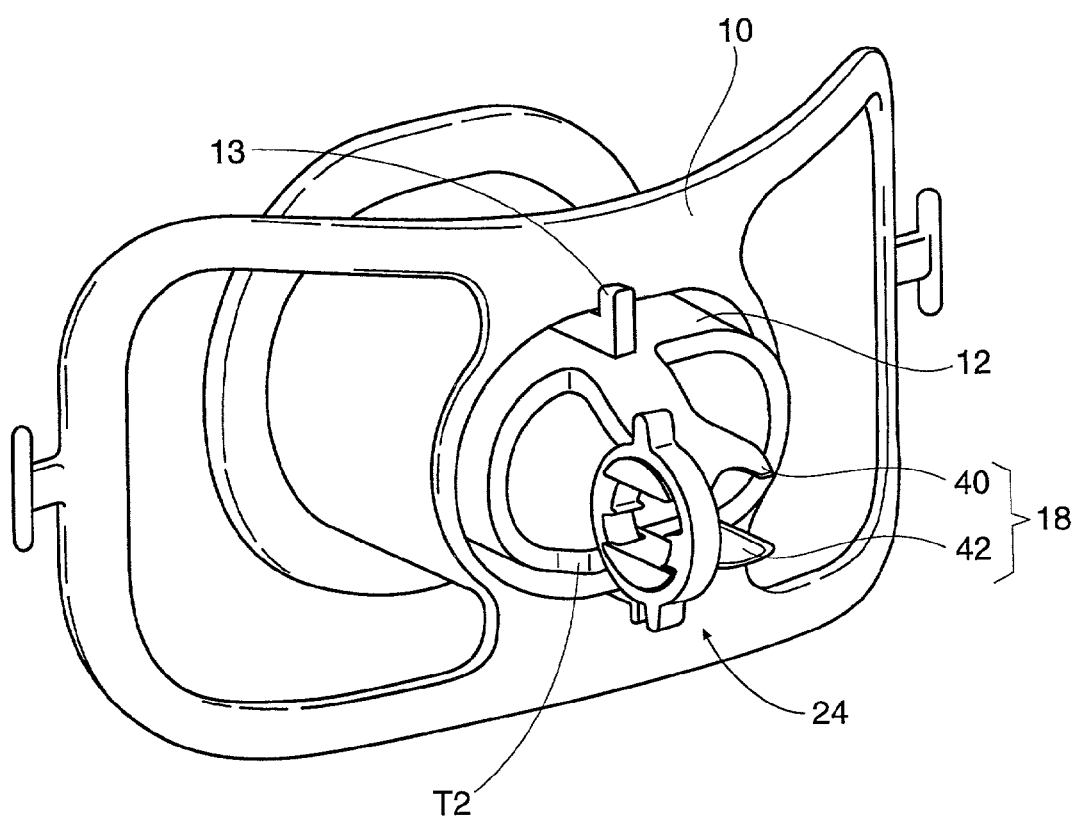
FIG. 2 is a front view of a bite block incorporating an insert carrying a gripping tool with a cam mechanism.

FIG. 1a-a/1a-b, 1b, and 1c show eight representative embodiments of gripping tools, T1 to T8, each taking the form of an insert 12 insertable into the bite block opening 11. FIG. 2 shows a bite block 10 carrying one embodiment of the gripping tool (T2) after insertion into the bite block 10.

In any one of the embodiments of the gripping tool, T1 to T8 shown in FIGS. 1a-a/1a-b, 1b, and 1c, the inserts 12 may be formed, e.g., from hard, medical grade plastic by conventional molding techniques.

In the illustrated embodiments T1–T6, the insert 12 is a generally cylindrical hollow body constructed to couple to the bite block 10 upon insertion. As shown in FIGS. 1a-a/1a-b and 1b, in the illustrated embodiments T1–T6, the insert 12 comprises at least three features that serve to secure and guide the insert into the proper position within the bite block opening 11.

First, as shown in FIG. 1a-a/1a-b, the insert 12 includes a top vane 14 and a bottom vane 23 that extend the length of the insert 12. The vanes 14 and 23 are tapered so as to secure the insert 12 in proper position within the bite block 10 by making friction fit engagement against the interior wall of the bite block opening 11.

Alternately, as shown in FIG. 1b, a second top vane 14 and a second bottom vane 23 may be provided.

Second, the insert 12 includes a stoprest 13 to prevent over insertion of the gripping tool (T). The stoprest 13 is a straight perpendicular extension of the front edge of any of the vanes 14 or 23.

In the embodiments T1 to T5 shown in FIG. 1a-a/1a-b, the stoprest 13 is located on the top vane 14. In the embodiment T6 shown in FIG. 1b, the stoprests 13 are located on both top vanes 14 and bottom vanes 23.

Of course, any number of vanes 14 and 23 and stoprests 13 can be provided.

Third, to further secure the insert 12 properly within the bite block opening 11, the insert 12 also includes first and second lips 16 on opposing sides of the insert 12. The lips 16 have a plastic memory so as to engage the rear edge of the bite block 10 in a snap fit when the insert 12 is properly positioned within the bite block opening 11.

In alternate embodiments T7 and T8 (see FIG. 1c), an alternate insert 12' is provided that incorporates a "clip-on" type mechanism constructed to couple to the bite block 10 upon insertion. FIGS. 10c–10d illustrate a bite block 10 carrying one embodiment (T7) of the clip-on insert 12' after insertion into the bite block 10.

Figure 11A:
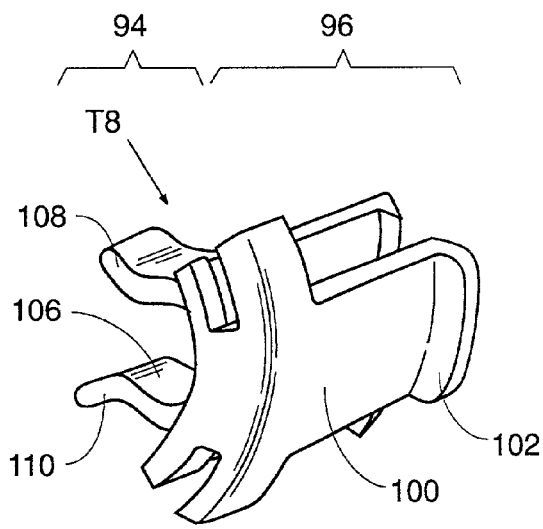
FIG. 11a is a side view of a bite block and an embodiment of a clip-type insert shown in FIG. 11c that may be employed with the bite block.
Figure 11B:
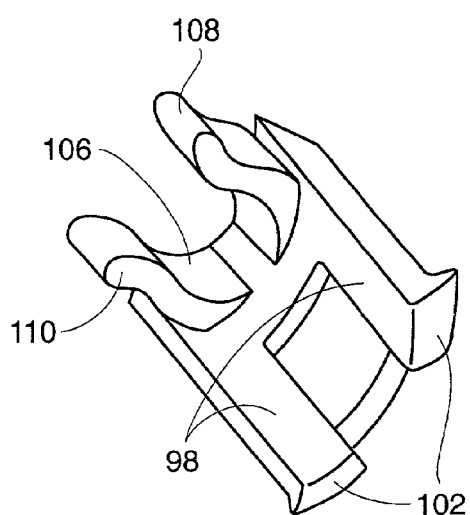
Figure 11C:
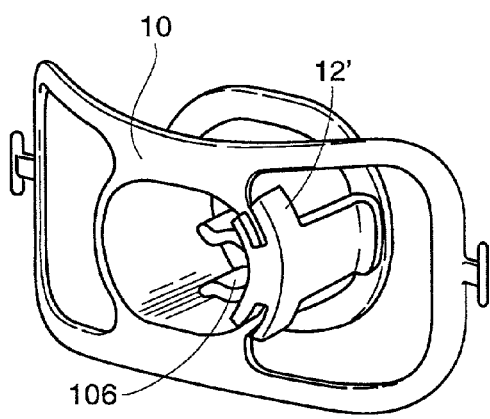
Figure 11D:
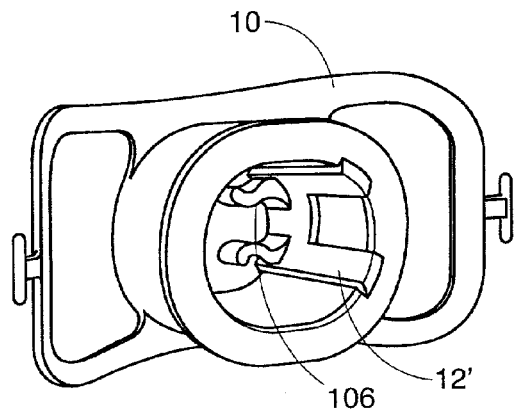
FIG. 11d is rear view of the bite block and incorporated insert shown in FIG. 11c.

FIGS. 11c and 11d illustrate a bite block 10 carrying another embodiment (T8) of the clip-on insert 12' after insertion into the bite block 10.

In the illustrated embodiments T7–T8, as shown in FIGS. 10a–10d and 11a–11d, the insert 12' comprises at least three features that serve to secure and guide the insert 12' into the proper position within the bite block opening 11.

First, as shown in FIGS. 11a and 11b, the insert 12' is a member having a "folded" or "curved" shape whereby the insert 12' is adapted to slide over the wall of the bite block 10 on either the right or left side of the opening 11. In this arrangement, the "fold" or curve" results in the insert 12' having a first side 94 and a second side 96.

The first side 94 of the insert 12' is adapted to be positioned in the interior of the opening 11 and rest against the bite block 10 wall when the insert 12' is positioned within the bite block 10 (see FIGS. 11c and 11d). The first side 94 carries a jaw assembly 18. The second side 96 is adapted to be positioned exterior to opening 11 and rest against the bite block 10 wall when the insert 12 is positioned within the bite block 10.

Second, the insert 12' is curved to prevent rotation within the bite block 10. In the embodiments illustrated in FIGS. 10a–10d and 11a–11d, the opening 11 is generally oval shaped. The insert 12' is shaped so as to match the curvature of the bite block 10 on the right or left side of the bite block 10, but not necessarily the top or bottom of the bite block 10.

This arrangement results in the gripping tool (T) having an eccentric location (see FIGS. 10c and 11c). The eccentric location provides a larger area in which to insert the external instrument 15 before positioning it within the gripping tool (T). The insertion of an external instrument 15 within a bite block 10 carrying an eccentrically located gripping tool (T) is illustrated in FIGS. 12 and 13.

Figure 12:
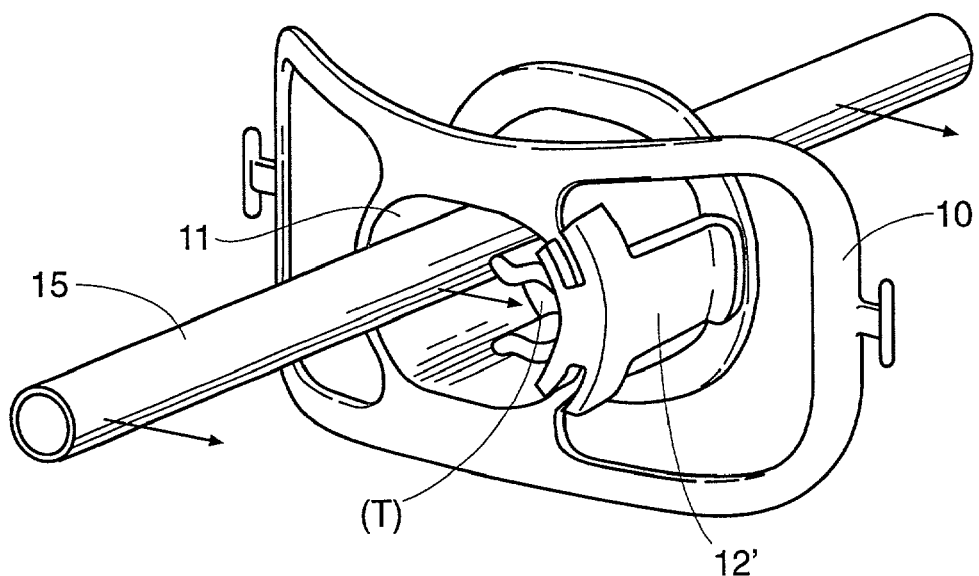
FIG. 12 is a front view of a bite block, showing the insertion of an external instrument through the opening of the bite block alongside a jaw assembly and illustrating the movement required to position the external instrument in the jaw assembly.

As shown in FIG. 12, an external instrument 15 is inserted within the bite block opening 11. As indicated by arrows in FIG. 12, the external instrument 15 can then moved laterally to position it within the gripping tool (T).

Figure 13:
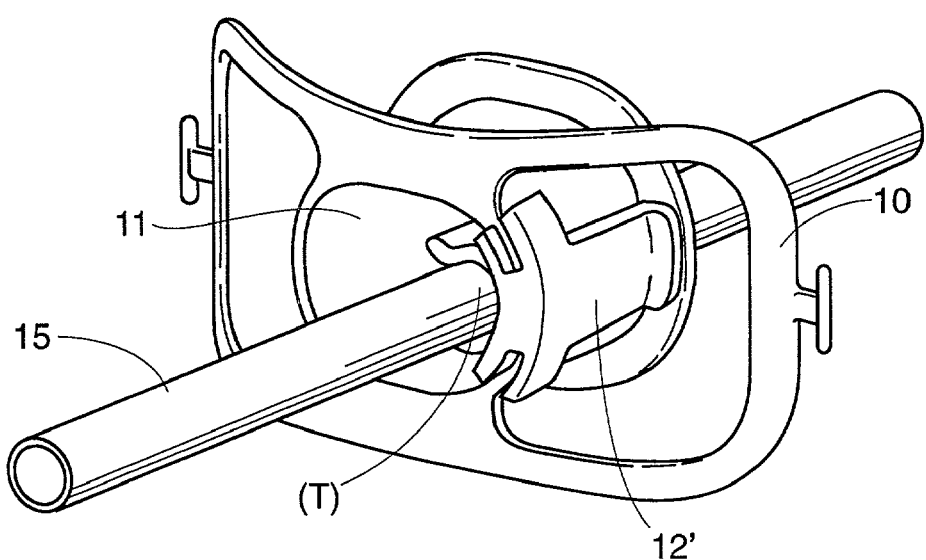
FIG. 13 is a front view of a bite block as in FIG. 12, illustrating the positioning of the external instrument in the jaw assembly.

FIG. 13 illustrates the external instrument 15 positioned within the gripping tool (T).

Third, the insert 12' contains opposed grasping clasps positioned on opposite interior and exterior sides of the bite block 10 wall. Of course, the construction and number of grasping clasps can vary.

Figure 10A:
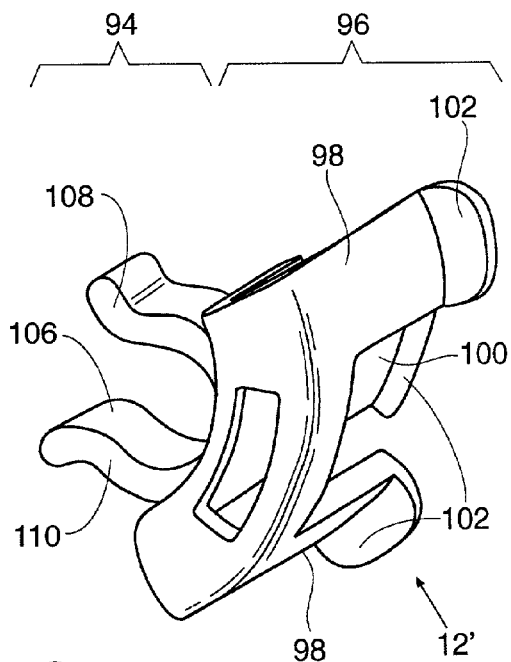
FIG. 10a is a side view of a bite block and an embodiment of a clip-type insert shown in FIG. 1c that may be employed with the bite block.
Figure 10B:
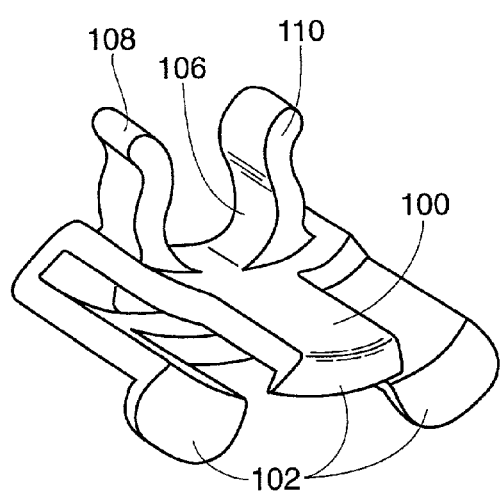
Figure 10C:
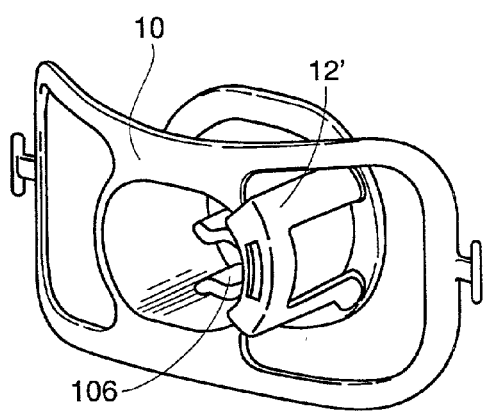
Figure 10D:
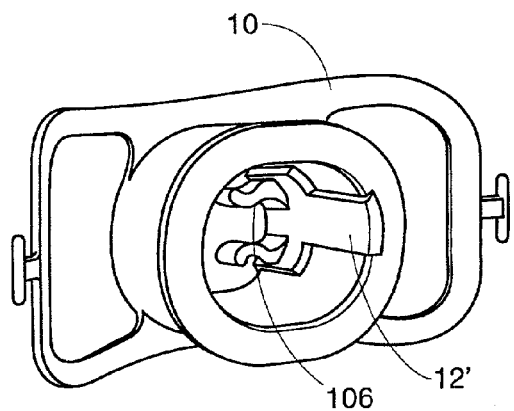
FIG. 10d is rear view of the bite block and incorporated insert shown in FIG. 10c.

In the embodiment illustrated in FIGS. 10*a* and 10*b*, two outer grasping clasps 98 are spaced parallel to each other and positioned to be on one side of the bite block 10 wall when the insert 12' is positioned within the bite block 10. An inner clasp 100 is positioned (desirably equidistant) between the outer clasps 98 and positioned to be on the opposite side of the bite block 10 wall from the outer clasps 98 when the insert 12' is positioned within the bite block 10.

Each of the clasps 98 and 100 has a foot-like appendage 102 extending perpendicularly from the end of the clasps 98 and 100. The foot-like appendages 102 are capable of abutting against the back wall of bite block 10 when the insert 12' is positioned within the bite block 10, such that they provide a snap fit when the insert 12' is positioned within the bite block 10.

Regardless of the particular structure, the purposes of the gripping tool (T) are to accommodate passage of an external instrument 15 through the bite block 10 and to grip the external instrument 15.

Figure 3A:
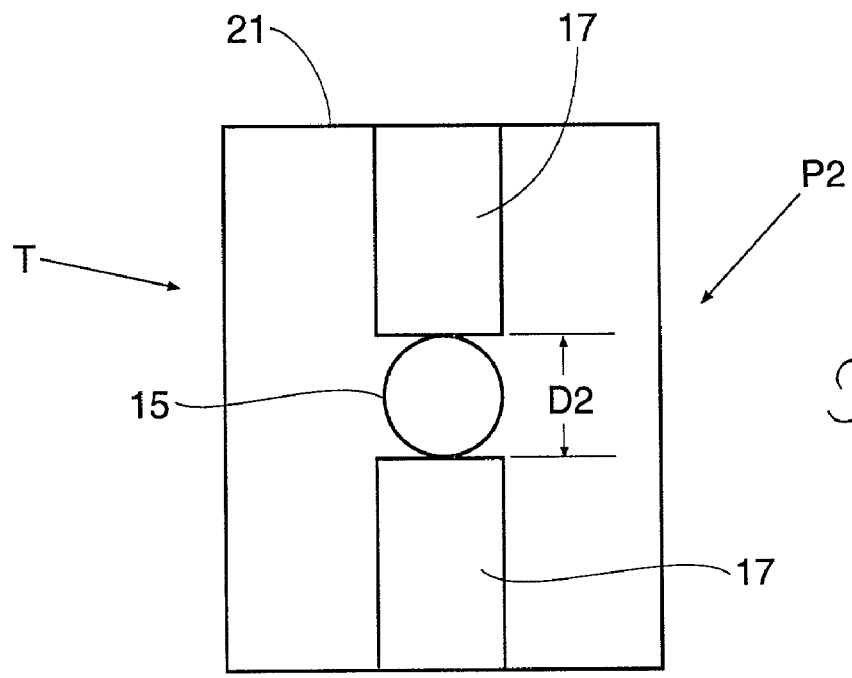
FIG. 3*a* is a schematic of a gripping tool showing the position of a gripping element and actuator mechanism in a closed position.
Figure 3B:
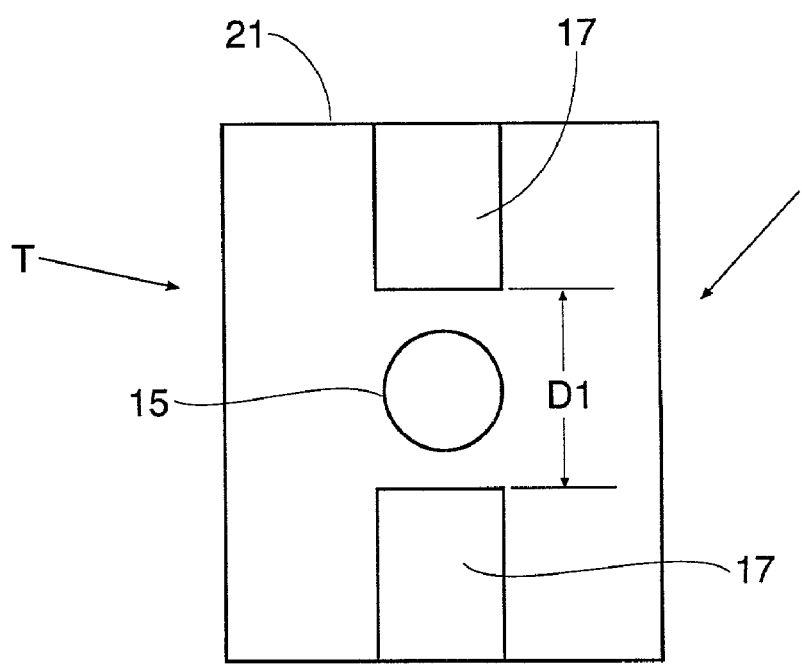
FIG. 3*b* is a schematic of a gripping tool showing the position of a gripping element and actuator mechanism in an open position.

To this end, as illustrated in FIGS. 3*a* and 3*b*, the gripping tool (T) comprises gripping elements 17 that are selectively movable and capable of pivoting between an open position (P1) (see FIG. 3*b*) and a closed position (P2) (see FIG. 3*a*), such that the distance between the elements 17 is greater in P1 than in P2. An actuator mechanism 21 effectuates movement of the elements between P1 and P2.

P1 (shown in FIG. 3*b*) is an open spaced-apart position corresponding to a first distance (D1) between the gripping elements 17. P2 (shown in FIG. 3*a*) is a closed adjacently-spaced position corresponding to a second distance (D2) between the gripping elements 17, such that D2 is less than D1.

As FIG. 3*b* shows, in P1 the gripping tool (T) accommodates passage of an external instrument 15 through the bite block 10. As FIG. 3*a* shows, in P2 the gripping tool (T) contacts the periphery of the external instrument 15, thereby maintaining the instrument 15 in a fixed position within the bite block 10.

As FIGS. 1*a-a*/1*a-b*, 1*b*, and 1*c* demonstrate, and as has already generally been discussed, the gripping tool (T) may take a variety of embodiments, eight of which (T1 to T8) are shown in FIGS. 1*a-a*/1*a-b*, 1*b*, and 1*c*. Other embodiments, of course, are possible.

A. Bite Block Embodiment T1

FIGS. 4*a*–4*e* detail one of the embodiments (T1) shown in FIG. 1*a* and its use. In the embodiment illustrated in FIG. 4*a*, the gripping element 17 consists of a jaw assembly 18 carried by the insert 12. The jaw assembly 18 comprises a first jaw 40 and a second jaw 42. The jaws 40 and 42 extend from the insert 12 at parallel and oppositely spaced locations, thus having interior facing surfaces and exterior non-facing surfaces relative to each other.

In the illustrated embodiment, resilient plastic memory biases the jaws 40 and 42 toward the closed position P2. The relative positions of the jaws 40 and 42 in Pi (phantom lines) and P2 (solid lines) are illustrated in FIG. 4*e*.

As shown in FIGS. 4*a*–4*d*, each of the jaws 40 and 42 includes a first indented cam surface 20 and a pair of second raised cam surfaces 22 on each jaw 40 and 42 flanking the indented cam surface 20.

The first cam surface 20 comprises an area of reduced thickness in the wall of the jaws 40 and 42. The first cam surfaces 20 are normally oppositely spaced at the second distance D2, as FIG. 4*d* shows, to normally grip the instrument 15 confined between the jaws 40 and 42, corresponding to position P2.

The second cam surfaces 22 comprise areas of greater thickness in the walls of the jaws 40 and 42.

As FIG. 4*c* shows, manipulation of an external instrument 15 between an opposing pair of second cam surfaces 22 causes the jaws 40 and 42 to yield and open. The first cam surfaces 20 are moved to the first distance D1, corresponding to position P1, thereby allowing the external instrument 15 to be inserted between the jaws 40 and 42 and removed from the jaws 40 and 42.

In this embodiment, the jaws 40 and 42 are formed to include the resilient plastic memory that, together with the cam surfaces 20 and 22, provides the actuator mechanism 21 for the jaws 40 and 42. The combination of the plastic memory and the cam surfaces 20 and 22 enables the jaws 40 and 42 to be moved so as to pivot selectively between P1 and P2.

More particularly, the resilient plastic memory yields in response to contact between the instrument 15 and the second cam surfaces 22 to allow the external instrument 15 to be inserted between the jaws 40 and 42 (position P1 to P2) and, likewise, to be removed from the jaws 40 and 42 (position P2 to P1).

In the closed position, the jaws 40 and 42 are capable of holding an external instrument 15 in a fixed position. In the open position, the jaws 40 and 42 are positioned such that the external instrument 15 is not held in a fixed position, allowing it to be inserted or removed.

In the illustrated embodiment, the jaws 40 and 42 are carried by an insert 12. Alternately, the jaws 40 and 42 may be integral with a bite block 10.

B. Bite Block Embodiment T2

FIGS. 5*a*–5*i* detail a second embodiment (T2) of the gripping tool shown in FIG. 1*a* and its use. In the embodiment illustrated in FIG. 5*a*, the gripping element 17 consists of a jaw assembly 18. The jaw assembly 18 comprises a first jaw 40 and a second jaw 42 carried by the insert 12. The jaws 40 and 42 are similar to the jaws 40 and 42 in FIGS. 4*a*–4*e*, but need not contain first cam surfaces 20 or second cam surfaces 22.

In this embodiment, the actuator mechanism 21 includes a resilient plastic memory in the jaws 40 and 42 and a cam mechanism 24 coupled to the jaws 40 and 42. In the illustrated embodiment, this resilient memory biases the jaws 40 and 42 toward the P1, or open position shown in FIGS. 5*d*–5*f*. Engagement of a series of cam regions on the control knob 26 by manipulation of the cam mechanism 24 overcomes this bias and moves the jaws 40 and 42 from the open (P1) position to the closed (P2) position, shown in FIGS. 5*g*–5*i*.

Alternately, the resilient memory can bias the jaws 40 and 42 in the P2, or closed, position. In yet another alternate embodiment, the jaws 40 and 42 need not be biased in either position.

A variety of cam mechanisms 24 can be utilized. The cam mechanism 24 can be conventional, formed, e.g., from hard, medical grade plastic by conventional molding techniques.

FIG. 5*b* illustrates an embodiment in which the cam mechanism 24 includes a control knob 26 and a pair of control appendages 28. As FIG. 5*a* shows, the control appendages 28 are connected to the jaws 40 and 42 and engage the control knob 26. The control knob 26 rotates on the appendages 28.

Each jaw 40 and 42 includes a control appendage 28 that extends from the respective jaw 40 or 42 in a perpendicular direction, as best illustrated in FIGS. 5b–5c. Rotation of the control knob 26 exerts force on the control appendages 28 and thereby opens and closes the jaws 40 and 42 (i.e., moves the jaws 40 and 42 selectively between P1 and P2).

In the illustrated embodiment (see FIG. 5b), the control knob 26 takes a ring form having an interior surface and an exterior surface. The interior surface includes a pair of diametrically opposed first cam regions 30. A pair of diametrically opposed second cam regions 32 are oppositely spaced in the interior surface at a decreased diameter relative to the first cam regions 30.

The control appendages 28 rest within the interior surface of the control knob 26 in contact with either the first cam regions 30 or the second cam regions 32. Rotation of the control knob 26 in a first direction (counterclockwise as shown by arrow in FIG. 5d), brings the first cam regions 30 into contact with the appendages 28.

Figure 5D:
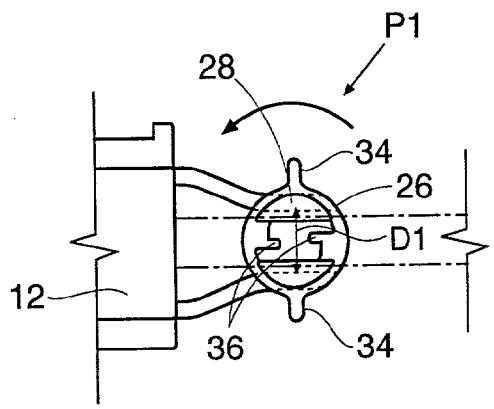
FIG. 5*d* is a side view of the insert shown in FIG. 5*a*, illustrating the position of the cam mechanism in the open position.
Figure 5G:
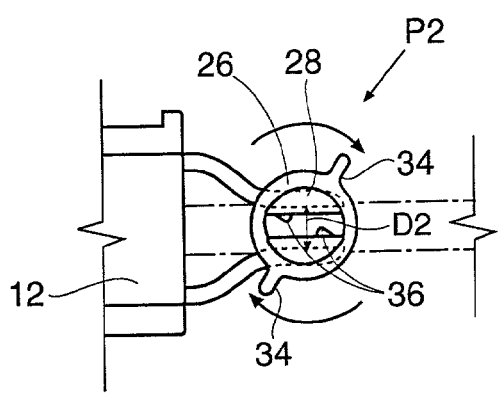
FIG. 5*g* is a side view of the insert shown in FIG. 5*a*, illustrating the position of the cam mechanism in the closed position.
Figure 5E:
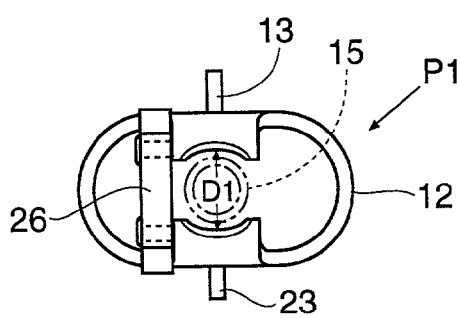
FIG. 5*e* is a front view of the insert shown in FIG. 5*a*, illustrating the position of the jaws of the gripping tool in the open position.
Figure 5H:
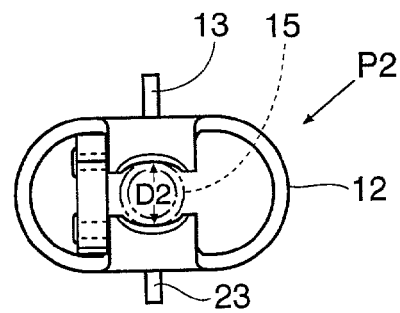
FIG. 5*h* is a front view of the insert shown in FIG. 5*a*, illustrating the position of the jaws of the gripping tool in the closed position.
Figure 5F:
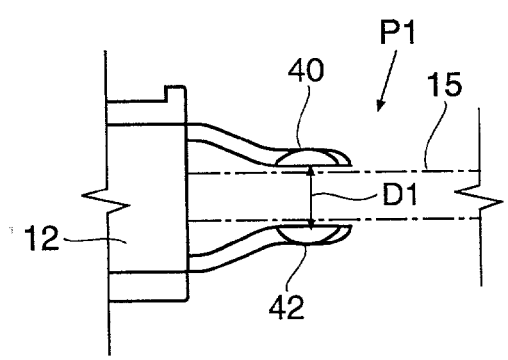
FIG. 5*f* is a side view of the insert shown in FIG. 5*a*, illustrating the position of the jaws of the gripping tool in the open position.

When the appendages 28 rest in contact with the first cam regions 30, the jaws 40 and 42 assume their normally biased open spaced-apart position (P1), corresponding to a first distance (D1) between the jaws 40 and 42. The position of the cam in the P1 position is shown in FIG. 5d. The corresponding positioning of the jaws 40 and 42 in the P1 position is shown in FIGS. 5e–5f.

In the open position (see FIGS. 5e and 5f), the jaws 40 and 42 are positioned such that the external instrument 15 is not held in a fixed position, allowing it to be inserted or removed.

Rotation of the control knob 26 in a second direction (clockwise as shown by arrow in FIG. 5g) brings the second cam regions 32 into contact with the appendages 28.

Figure 5I:
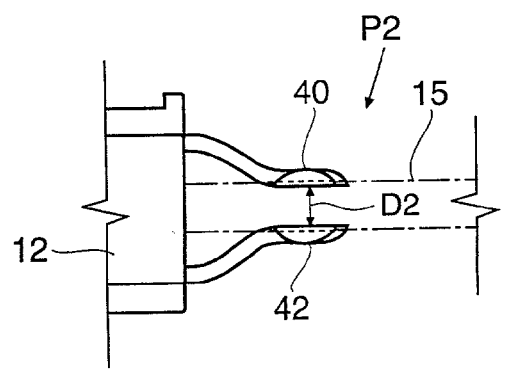
FIG. 5*i* is a side view of the insert shown in FIG. 5*a*, illustrating the position of the jaws of the gripping tool in the open position.

When the control appendages 28 rest in contact with the second cam regions 32, the jaws 40 and 42 are moved against the biasing force into the closed adjacently-spaced position (P2), corresponding to a second distance (D2) between the jaws 40 and 42, such that D2 is less than D1. The position of the cam in the P2 position is shown in FIG. 5g. The corresponding positioning of the jaws 40 and 42 in the P2 position is shown in FIGS. 5h–5i.

In the closed position (see FIGS. 5h and 5i), the jaws 40 and 42 are capable of holding an external instrument 15 in a fixed position.

As best illustrated in FIG. 5b, the control knob 26 desirably includes first and second grasping extensions 34 to aid in the rotation of the control knob 26 circumferentially upon the appendages 28.

A first and second stopguard 36 (see FIG. 5b) are also desirably provided. The stopguards 36 prevent over-rotation of the control knob 26 in the first and second directions.

Rotation thus permits the control knob 26 to move selectively between P1, in which the control appendages 28 contact the first cam regions 30, and P2, in which the control appendages 28 contact the second cam regions 32, thus permitting the jaws 40 and 42 to pivot between the D1 and D2 positions. In P2, the first stopguard 36 rests against the first control appendage 28 and the second stopguard 36 rests against the second control appendage 28.

In P1, the first stopguard 36 does not contact the first control appendage 28 and the second stopguard 36 does not contact the second control appendage 28. However, further rotation in the first direction beyond Pi is prevented by contact between the stopguards 36 and their opposing control appendage 28.

In the illustrated embodiment, the cam mechanism 24 and jaws 40 and 42 are carried by an insert 12 for a bite block 10. Alternately, the cam mechanism 24, the jaws 40 and 42, or both may be integral with the bite block 10.

C. Bite Block Embodiment T3

FIGS. 6a–6e detail another embodiment (T3) shown in FIG. 1a and its use. In the embodiment illustrated in FIG. 6a, the gripping element 17 takes the form of jaw assembly 18 comprising a "C-clamp" 38 carried by the insert 12.

Figure 6A:
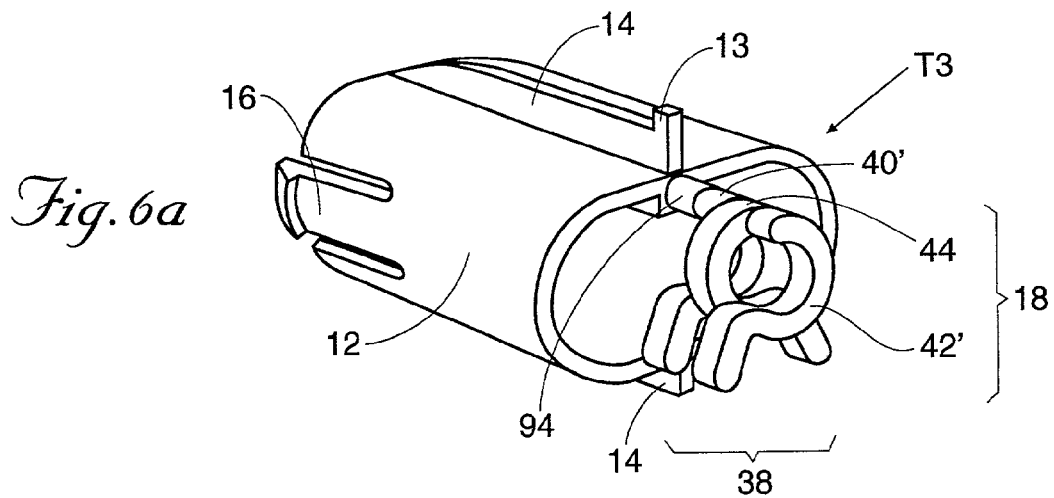
FIG. 6*a* is a side view of an embodiment shown in FIG. 1*a*-*a* that incorporates a C-clamp mechanism.
Figure 6B:
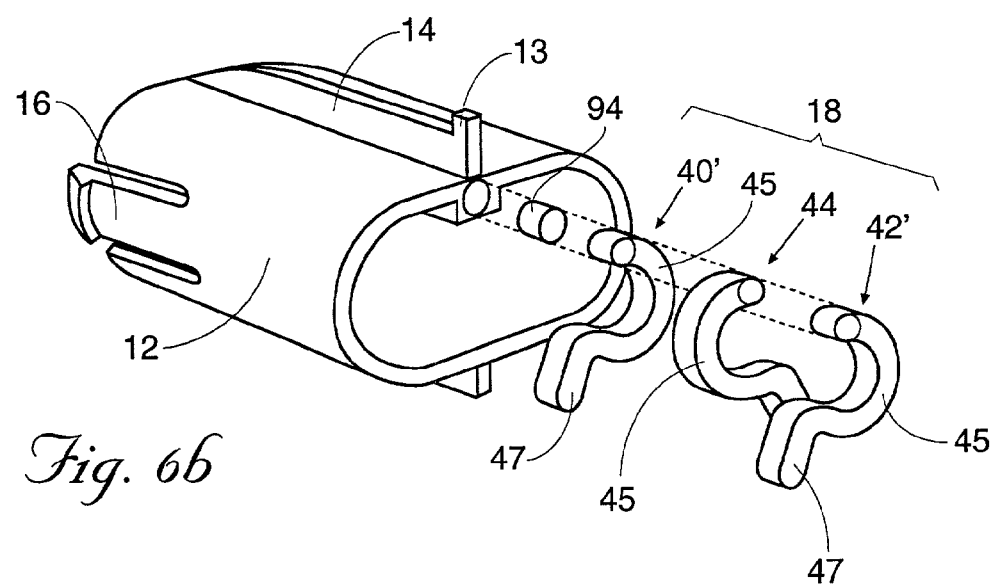
FIG. 6*b* is an exploded view of FIG. 6*a*.
Figure 6C:
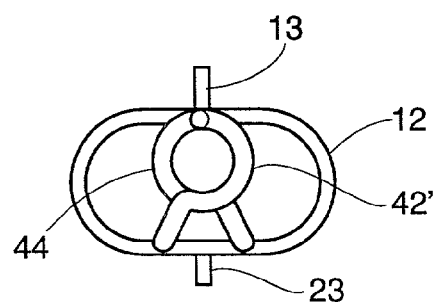
FIG. 6*c* is a front view of the insert shown in FIG. 6*a*.

As FIGS. 6a–6c best show, this C-clamp 38 includes levers comprising a first jaw 40', a second jaw 42', and a third jaw 44. The jaws 40', 42', and 44 each include a first region 45 and second region 47.

The first region 45 is generally semi-circle-shaped. The second region 47 is a straight appendage extending from the end of the first region 45 and serves as a grasping appendage.

The third jaw 44 is a mirror image of the first jaw 40' and the second jaw 42' also having a first region 45 and a second region 47.

As shown in FIG. 6b, the C-clamp 38 also comprises a post 94 extending from the top of the front surface of the insert 12. The post 94 extends through corresponding points on the first region 45 of each jaw 40', 42', and 44. Thus, the post 94 serves as an axis upon which the jaws 40', 42', and 44 are attached in a hinged fashion such that they may pivot selectively along the axis of the post 94.

The first jaw 40' is positioned proximal to the front surface of the insert 12 along the axis of the post 94. The third jaw 44 is positioned medially along the axis of the post 94. The second jaw 42' is positioned distally along the axis of the post.

Figure 6D:
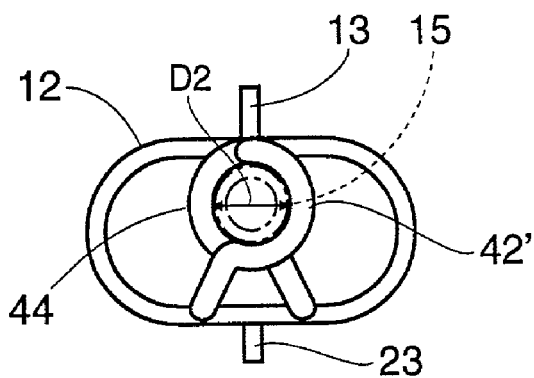
FIG. 6*d* is a front view of the insert shown in FIG. 6*a*, illustrating the position of the jaws of the gripping tool in the closed position.
Figure 6E:
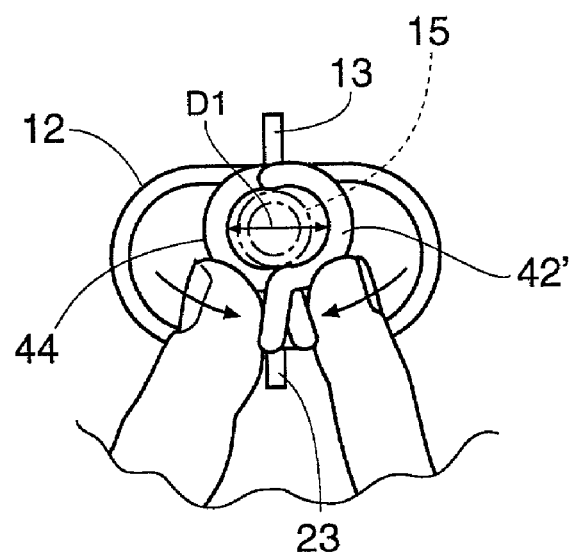
FIG. 6*e* is a front view of the insert shown in FIG. 6*a*, illustrating the use of the C-clamp and the position of the jaws of the gripping tool in the open position.

The hinged arrangement permits the jaws 40', 42', and 44 to pivot between a first position (P1) (see FIG. 6e) and a second position (P2) (see FIG. 6d).

In P1, the second region 47 of the third jaw 44 is aligned with the second regions 47 of the first jaw 40' and the second jaw 42'. In this position, the three first regions 45 form an opening of a first diameter (D1). This corresponds to an open position, in which an external instrument 15 is not able to be held in a fixed position.

In P2, the second region 47 of the third jaw 44 is spaced apart from the second regions 47 of the first jaw 40' and the second jaw 42'. In this position, the first regions 45 of the three jaws form an opening of a second diameter (D2), such that D2 is less than D1. This corresponds to a closed position, in which an external instrument 15 can be held in a fixed position.

The hinge mechanism provides a resilient plastic memory and serves as an actuator mechanism 21 that enables the jaws 40', 42', and 44 to be moved so as to pivot selectively between P1 and P2. This resilient memory biases the jaws 40', 42', and 44 toward the closed position P2 (see FIG. 6d). Application of "squeezing" pressure (illustrated by arrows in FIG. 6e) on the second regions of the jaws 40', 42', and 44 overcomes this bias and moves the jaws 40', 42', and 44 from the closed (P2) position to the open (P1) position.

The C-clamp 38 may be conventional, formed, e.g., from hard, medical grade plastic by conventional molding techniques.

In the illustrated embodiment, the C-clamp 38 is carried by an insert 12 for a bite block 10. Alternately, the C-clamp 38 or any portion of it may be integral with the bite block 10.

D. Bite Block Embodiment T4

FIGS. 7a–7e detail another embodiment (T4) shown in FIG. 1a and its use. In the embodiment illustrated in FIG. 7a, the gripping element 17 takes the form of jaw assembly 18 comprising a "prong-clamp" carried by the insert 12.

As FIGS. 7a–7c show, this prong-clamp 38 comprises a first jaw 40 and a second jaw 42. The jaws 40 and 42 are similar to the jaws 40 and 42 in FIGS. 4a–4e, but need not contain first cam surfaces 20 or second cam surfaces 22.

As shown in FIG. 7a, this prong-clamp 46 also includes levers comprising a first prong 52, a second prong 54, and a third prong 56.

As also shown in FIG. 7a, the first prong 52 and second prong 54 are integral with the first jaw 40. The prongs consist of a first section 48 and a second section 50. The first section 48 extends perpendicularly from the first jaw 40 at a right angle. The second section 50 extends perpendicularly from the first section 48 at a right angle from the first section 48.

The first prong 52 and second prong 54 are spaced apart along the first jaw 40 and positioned such that they are parallel to each other.

As shown in FIG. 7b, the third prong 56 is integral with the second jaw 42 and is spaced (desirably equidistant) between the first prong 52 and the second prong 54. The third prong 56 consists of a first section 48 and a second section 50 and is essentially a mirror image of the first prong 52 and second prong 54.

That is, the first section 48 extends perpendicularly from the second jaw 42 at a right angle. The second section 50 extends perpendicularly from the first section 48 at a right angle from the first section 48 and serves as a grasping appendage.

The jaws 40 and 42 possess a resilient plastic memory that serves as an actuator mechanism 21 that enables the jaws 40 and 42 to be moved so as to pivot selectively between P1 and P2.

In the open (P1) position, illustrated in FIG. 7e, the second section 50 of the third prong 56 is aligned with the second sections 50 of the first prong and the second prong 54. In this position, the three prongs impart a correspondingly spaced-apart relation to the jaws 40 and 42 corresponding to a first diameter (D1). This corresponds to an open position, in which an external instrument 15 is not able to be held in a fixed position.

In P2, illustrated in FIG. 7d, the second section 50 of the third prong 56 is spaced apart from the second sections 50 of the first prong 52 and the second prong 54. In this position, the three prongs impart a correspondingly spaced-apart relation to the jaws 40 and 42 corresponding to a second diameter (D2), such that D2 is less than D1. This corresponds to a closed position, in which an external instrument 15 can be held in a fixed position.

The resilient plastic memory biases the jaws 40 and 42 toward the closed, or P2 position. Application of "squeezing" pressure (illustrated by arrows in FIG. 7e) on the second sections 50 of the prongs 52, 54, and 56 overcomes this bias and moves the jaws 40 and 42 from the closed (P2) position to the open (P1) position.

The prong clamp 46 may be conventional, formed, e.g., from hard, medical grade plastic by conventional molding techniques.

In the illustrated embodiment, the prong-clamp 46 and jaws 40 and 42 are carried by an insert 12 for a bite block 10. Alternately, the prong-clamp 46 or any portion of it, the jaws 40 and 42, or any combination thereof may be integral with the bite block 10.

E. Bite Block Embodiment T5

FIGS. 8a–8g detail another embodiment (T5) shown in FIG. 1a and its use. In the embodiment illustrated in FIG. 8a, the gripping element 17 takes the form of a jaw assembly 18 comprising a "clothespin-type clamp" 104 carried by the insert 12.

As illustrated in FIGS. 8a–8g, this clothespin-clamp 104 comprises a C-shaped groove 106. The top side of the groove 106 comprises a first jaw 40 having an upturned edge 108. The bottom side of groove 106 comprises a second jaw 42 having a downturned edge 110. The upturned end downturned edges 108 and 110 serve as leading edges that guide the insertion of an external instrument 15 into the groove 104.

As shown in FIGS. 8a–8g, this clothespin-clamp 104 also includes a first arm 112 integral with and extending horizontally from the top of the C-shape and a second arm 114 integral with and extending horizontally from the bottom of the C-shape, positioned such that the first arm and second arms 112 and 114 are parallel to each other.

The jaws 40 and 42 possess a resilient plastic memory that, together with the upturned and downturned edges 106 and 108 and the first and second arms 112, serve as an actuator mechanism 21 that enables the jaws 40 and 42 to moved so as to pivot selectively between P1 and P2.

Figure 8A:
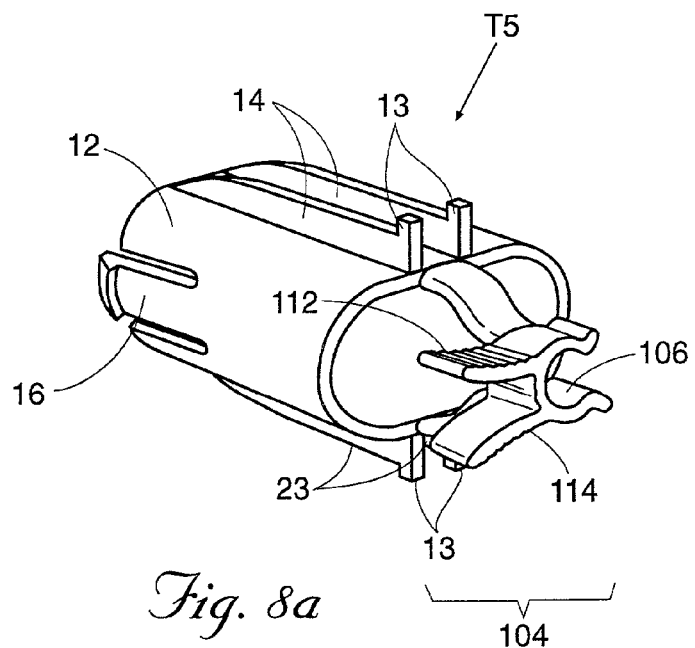
FIG. 8*a* is a side view of an embodiment shown in FIG. 1*a*-*b* that incorporates a clothespin-clamp mechanism centrally located within the insert opening.
Figure 8B:
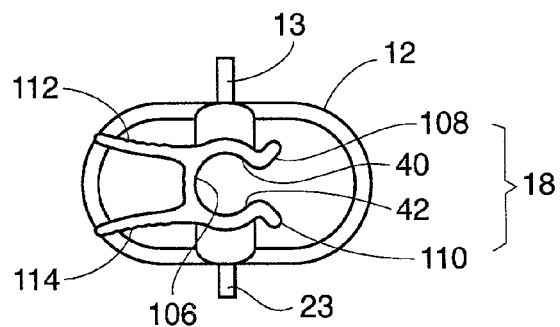
FIG. 8*b* is a front view of the insert shown in FIG. 8*a*.
Figure 8C:
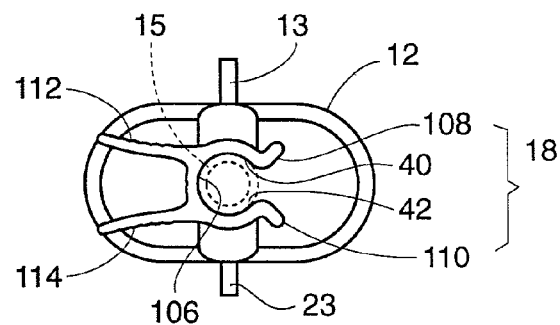
FIG. 8*c* is a front view of the insert shown in FIG. 8*a*, illustrating the position of the jaws of the gripping tool in the closed position.

This resilient plastic memory biases the jaws 40 and 42 toward the closed position P2 (shown in FIG. 8c).

Figure 8D:
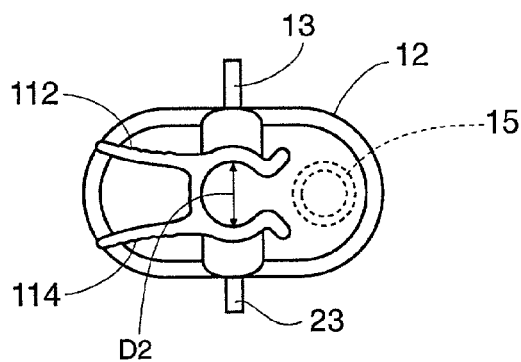
Figure 8D:
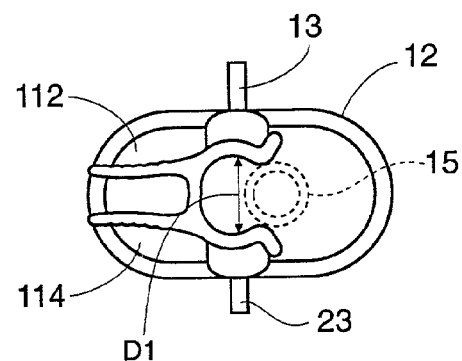
Figure 8F:
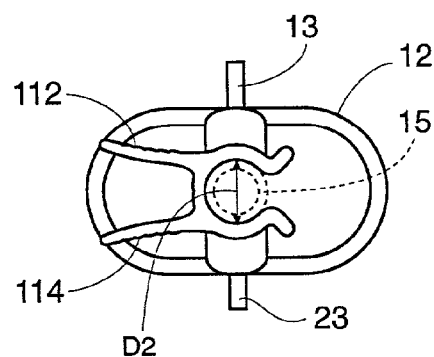

As illustrated in FIGS. 8d–8f, the resilient plastic memory yields in response to contact between the instrument 15 and the edges 108 and 110 to move the jaws 40 and 42 from the closed (P2) position to the open (P1) position.

Figure 8G:
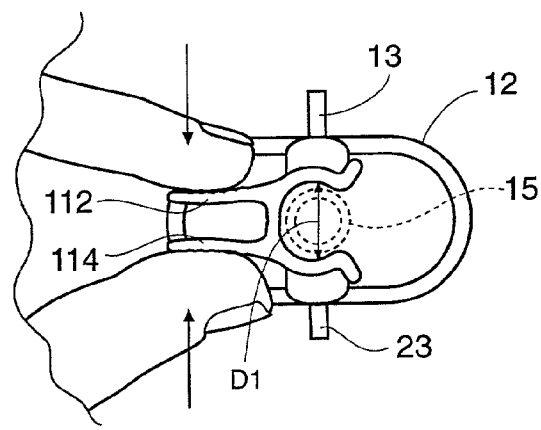
FIG. 8*g* is a front view of the insert shown in FIG. 8*a*, illustrating the use of the clothespin-clamp and the position of the jaws of the gripping tool in the open position.

As illustrated in FIG. 8g, application of "squeezing" pressure simultaneously on the first and second arms 112 and 114 (illustrated by arrows in FIG. 8g) also serves to overcome the bias and move the jaws 40 and 42 from the closed (P2) position to the open (P1) position.

In P1, the jaws 40 and 42 assume an open spaced-apart position corresponding to a first diameter (D1) between the jaws 40 and 42. This corresponds to an open position, illustrated in FIG. 8d and 8g, in which an external instrument 15 is not able to be held in a fixed position.

In P2, the jaws 40 and 42 assume their normally biased closed adjacently-spaced position corresponding to a second diameter (D2), such that D2 is less than D1. This corresponds to a closed position, best illustrated in FIG. 8f, in which the jaws 40 and 42 are capable of holding an external instrument 15 in a fixed position.

The clothespin-clamp 104 may be conventional, formed, e.g., from hard, medical grade plastic by conventional molding techniques.

In the illustrated embodiment, the clothespin-clamp 104 is carried by an insert 12 for a bite block 10. Alternately, the clothespin-clamp 104 or any portion of it may be integral with the bite block 10.

F. Bite Block Embodiment T6

Figure 9A:
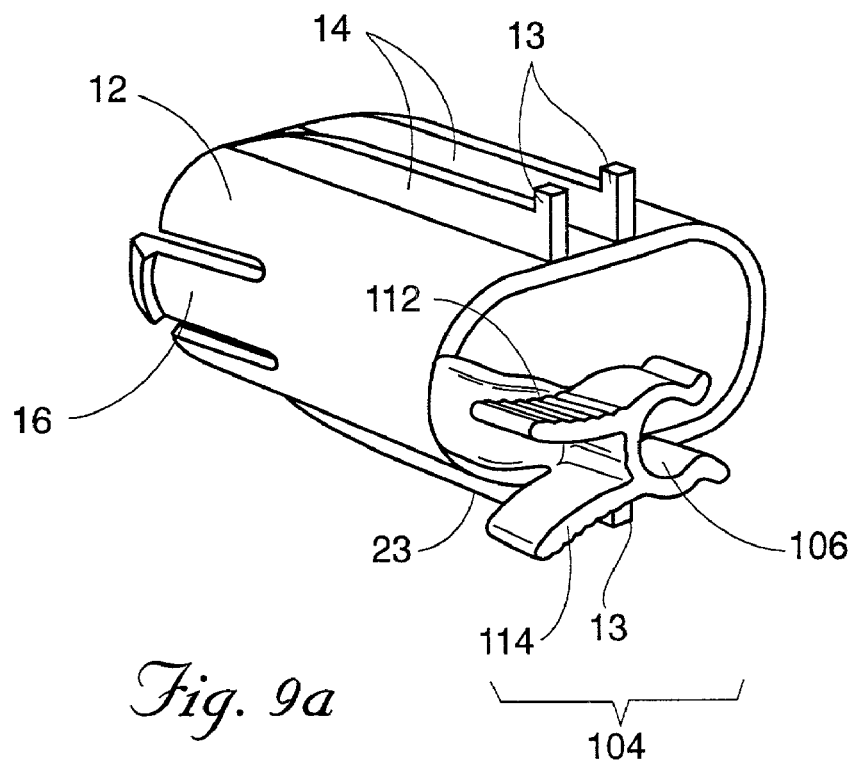
FIG. 9*a* is a side view of an embodiment shown in FIG. 1*b* that incorporates a clothespin-clamp mechanism eccentrically located within the insert opening.
Figure 9B:
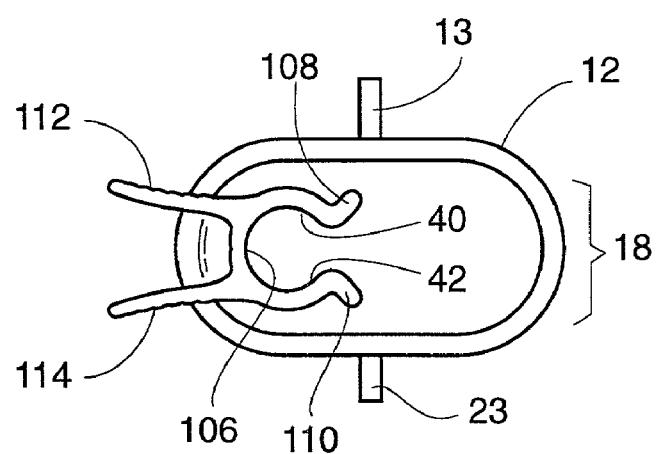
FIG. 9*b* is a front view of the insert shown in FIG. 9*a*.

FIGS. 9a and 9b detail another embodiment (T6) shown in FIG. 1b and its use. This embodiment is similar to embodiment T5, except that the jaw assembly 18 is adapted to be eccentrically located within the bite block opening 11 when the insert 12 is positioned within the bite block 10.

In the embodiments illustrated in T1–T5, the jaw assembly 18 is adapted so as to be centrally located within the bite block opening 11 when the insert 12 is positioned within the bite block 10.

Alternately, the jaw assembly 18 in any of the embodiments T1–T5 can be positioned so as to be eccentric, as in embodiment T6. As previously noted, an eccentric location provides for a larger area in which to insert the external instrument 15 before positioning it within the gripping tool (T).

G. Bite Block Embodiment T7

FIGS. 10*a*–10*d* detail another embodiment (T7) shown in FIG. 1*c* and its use.

The embodiment illustrated in FIG. 10*a* provides a C-shaped groove 106 functionally and structurally similar to that contained in embodiment T6. However, rather than a generally cylindrical hollow body insert 12, the C-shaped groove 106 is carried by a clip-on insert 12' as previously described. In this arrangement, the first and second arms 112 and 114 are not provided.

As best shown in FIGS. 10*b* and 10*d*, the first side 94 of the insert 12' includes the C-shaped groove 106. The groove 106 extends perpendicularly from the third clasp 100.

The groove 106 may be coated with an elastomeric material, making the groove 106 more tacky, thereby aiding in grasping an external instrument. This coating can be accomplished by either placing a tube over the groove 106 or placing a low durameter pad over the groove 106.

As best seen in FIGS. 10*a* and 10*c*, the second side 96 of the insert 12' includes the first and second clasps 98. In this arrangement, the first and second clasps 98 are positioned exterior to the opening 11 along the bite block 10 wall when the insert 12' is positioned within the bite block 10. The third clasp 100 and groove 106 are positioned interior to the opening 11 along the bite block 10 wall when the insert 12' is positioned within the bite block 10.

In the illustrated embodiment, the groove 106 is adapted to be positioned eccentrically within the opening 11 when the insert 12' is positioned within the bite block 10. Alternately, the insert 12' can be formed such that the groove 106 is positioned centrally within the opening 11 (not shown).

In the closed position (see FIG. 8*c*), the groove 106 is capable of holding an external instrument 15 in a fixed position. In the open position (see FIG. 8*e*), the groove 106 is positioned such that the external instrument 15 is not held in a fixed position, allowing it to be inserted or removed.

The C-shaped groove 106 may be conventional, formed, e.g., from hard, medical grade plastic by conventional molding techniques.

In the illustrated embodiment, the C-shaped groove 106 is carried by an insert 12' for a bite block 10. Alternately, the C-shaped groove 106 or any portion of it may be integral with the bite block 10.

H. Bite Block Embodiment T8

FIGS. 11*a*–11*d* detail another embodiment (T8) shown in FIG. 1*c* and its use.

The embodiment illustrated in FIG. 11*a* provides a C-shaped groove 106 mechanism on a clip-on type insert 12' as in embodiment T7.

As best illustrated in FIGS. 11*b* and 11*d*, the first side 94 of the insert 12' includes the C-shaped groove 106 as described for embodiment T7. However, the groove 106 extends perpendicularly from the first and second clasps 98 rather than from the third clasp 100.

As best illustrated in FIGS. 11*a* and 11*c*, the second side 96 of the insert 12' includes the third clasp 100. In this arrangement, the third clasp 100 is positioned exterior to the opening 11 along the bite block 10 wall when the insert 12' is positioned within the bite block 10. The first and second clasps 98 and groove 106 are positioned interior to the opening 11 along the bite block 10 wall when the insert 12' is positioned within the bite block 10.

As in embodiment T7, the groove 106 can be coated with an elastomeric material. While the illustrated embodiment shows an eccentric location, the groove 106 can be adapted to be centrally located within the opening 11 when the insert 11 is positioned within the bite block 10, as previously noted for embodiment T7.

II. Use of the Gripping Tool

Any one of the gripping tools (T1–T8) described can be used with a catheter 58 designed for the treatment of gastroesophageal reflux disease (GERD). One possible embodiment of such a catheter is shown in FIGS. 14*a* and 14*b*.

In the illustrated embodiment, a catheter 58 carries a series of electrodes 60 that, in use, can be coupled to a source of radio frequency energy to ohmically heat tissue and create a lesion in the tissue region, e.g., lower esophageal spinchter 90 (see FIG. 21*b*) or cardia 92 (see FIG. 30) or both. It has been discovered that natural healing of the lesions tightens the targeted and adjoining tissue.

Figure 14A:
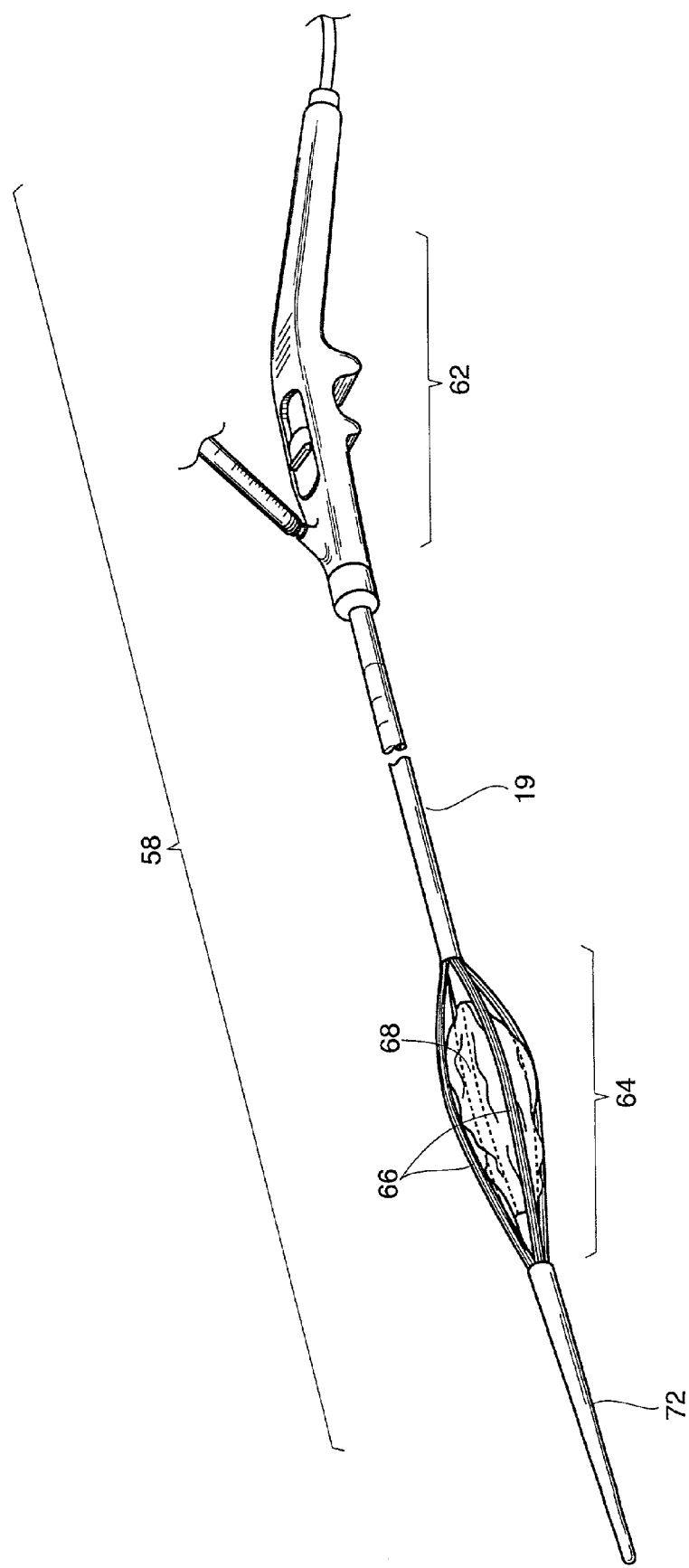
FIG. 14a is a side view of a catheter commonly employed in the treatment of GERD, illustrating an expandable structure in a deflated position and a series of electrodes retracted.
Figure 14B:
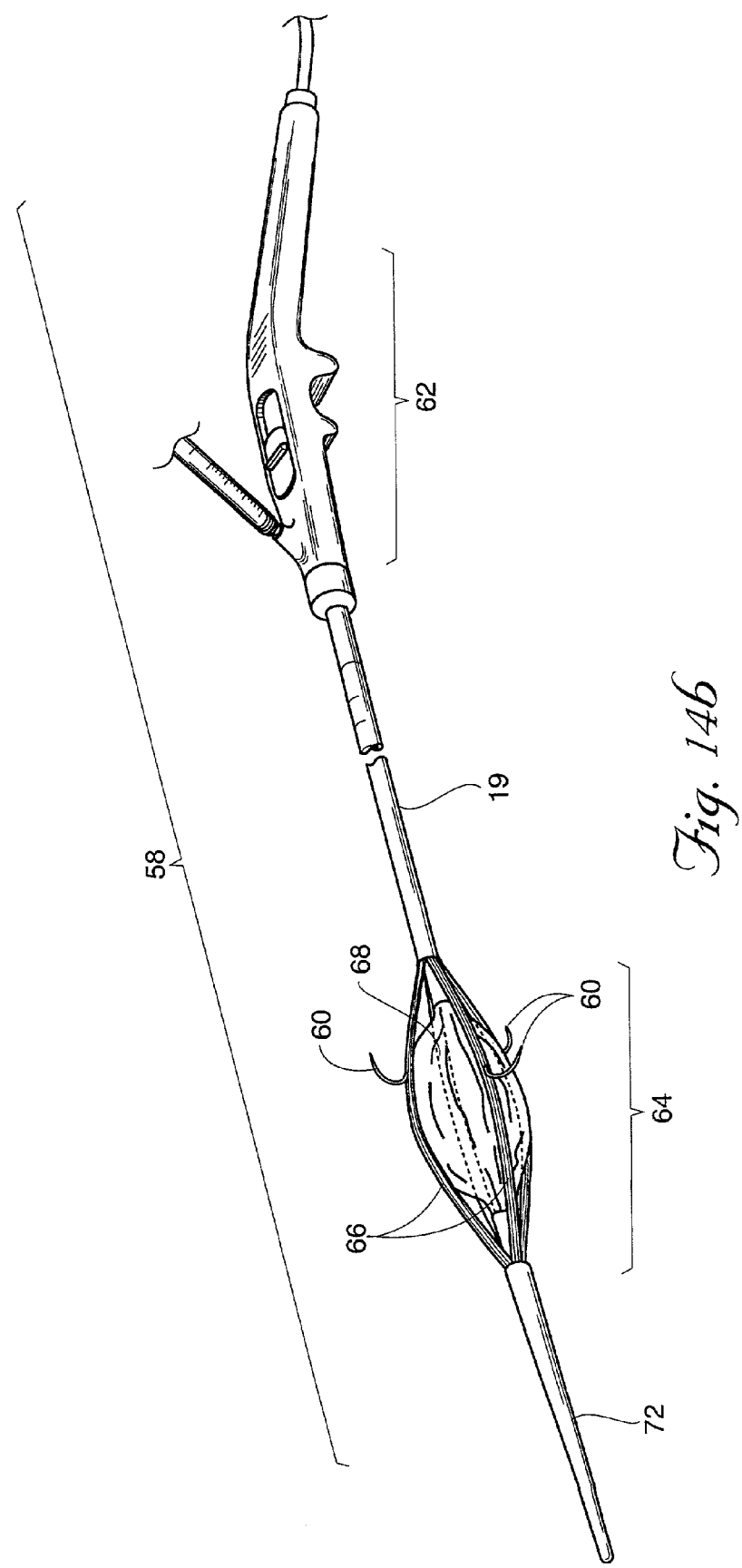
FIG. 14b is a side view of the catheter shown in FIG. 14a, illustrating the expandable structure inflated and the series of electrodes extended.
Figure 21B:
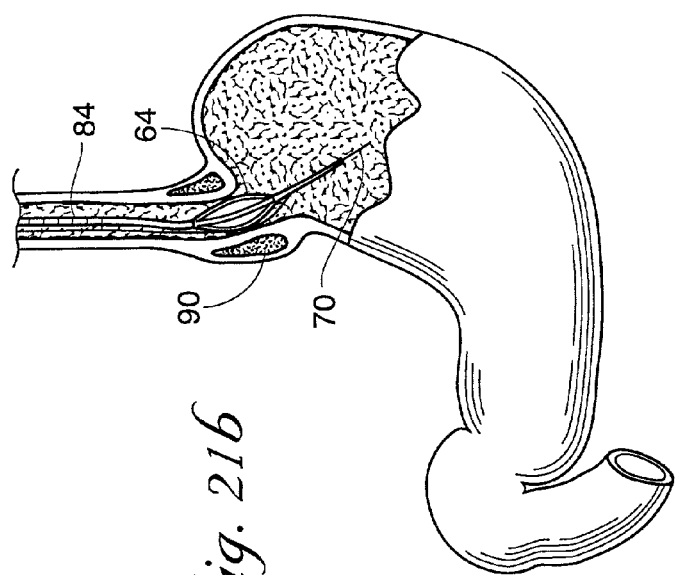
FIG. 21b is an enlarged side view of the lower esophagus and stomach showing the final positions of the guidewire and the catheter after employment.

FIGS. 14*a* and 14*b* show a representative embodiment for the catheter 58. Typically, the catheter 58 comprises a catheter tube 19 having a distal region and a proximal region. The proximal region includes a handle 62 incorporating control mechanisms. The distal region carries an expandable structure 64 (e.g., suitable for contacting the lower esophageal sphincter 90 during performance of procedures for the treatment of GERD, as shown in FIG. 21*b*).

As also shown in FIGS. 14*a* and 14*b*, the expandable structure 64 includes an array of tubular spines 66 that form a basket that is capable of being selectively expanded and contracted. The expandable structure 64 further comprises an expandable body 68 (e.g., balloon) within the basket.

The purpose of the expandable body 68 is to cause the basket to expand and contract within the esophagus 84. The expanded structure 64 serves to temporarily dilate the targeted tissue, thus removing some or all the folds normally present in the mucosal surface.

FIG. 14*a* shows the expandable structure 64 in the contracted or collapsed position. FIG. 14*b* shows the expandable structure 64 in the expanded position.

The electrodes 60 are carried within the spines 66 and are similarly capable of extension and retraction. The electrodes 60 are selectively movable between two positions. The first position is a retracted position, illustrated in FIG. 14*a*, in which they are withdrawn in a spine 66. The second position is an extended position, illustrated in FIG. 14*b*, in which they extend outward from the spine 66 through a hole in the spine 66.

The electrodes 60 can be biased with either an antegrade or retrograde bend. The electrodes 60 can also be arranged in bipolar pairs or in a singular, spaced-apart relation suitable for monopolar operation. In the illustrated embodiment, the electrodes 60 show an antegrade bend and a monopolar arrangement.

FIGS. 15*a* and 15*b* illustrate an embodiment in which the expandable structure 64 includes a distal tail 72 adapted to accommodate a guidewire 70. The purpose of the guidewire 70 is to aid insertion and guidance of the expandable structure 64 and catheter 58 through the oral cavity to a desired position within the esophagus 84 (see FIG. 21*a*). The configuration of the distal tail 72 eliminates the need to thread the guidewire 70 through the expandable structure 64 and the entire body of the catheter 58.

In the illustrated embodiment, the distal tail 72 extends approximately 3 inches (range=1 to 5 inches) beyond the distal end of the basket. The distal tail 72 may be conventional, formed, e.g., from semi-rigid, medical grade plastic (e.g., Pebax™, polyurethane, silicone, Santoprene™, or other flexible materials) by conventional molding techniques.

An interior lumen 74 extends through the distal tail 72. The interior lumen 74 is a passage that it does not communicate with any other lumen or structure within the body of the catheter 58. The purpose of the interior lumen 74 is strictly to permit passage of a guidewire 70. In an alternate embodiment, this lumen 74 could communicate with irrigation or aspiration lumens (not shown).

This interior lumen 74 terminates at the distal end in an opening 76 in the distal end of the tail 72. The interior lumen 74 terminates at the proximal end in an orifice 78 that penetrates the wall of the distal tail 72. In a representative embodiment, the orifice 78 is located approximately midway along the distal tail 72, or about one and one-half inches from the opening 76.

A slot 80 along the axis of the distal tail 72 is provided in the wall of distal tail 72. In a representative embodiment, the slot 80 extends approximately 1½ inches. The purpose of the slot 80 is to aid in threading a guidewire 70. The threading of a guidewire 70 through the slot 80 is illustrated in FIGS. 16*a* and 16*b*.

The orifice 78 is located at the distal end of the slot 80, such that the guidewire 70 is guided by the slot 80 as it is threaded through the orifice 78. The slot 80 does not penetrate the wall of the distal tail 72, thus it communicates with the interior lumen 74 in the distal tail 72 only through the orifice 78. The proximal end of the slot 80 tapers toward the exterior surface of the distal tail 72, thereby enabling it to guide the guidewire 70 as it is threaded through the distal tail 72.

Figure 17:
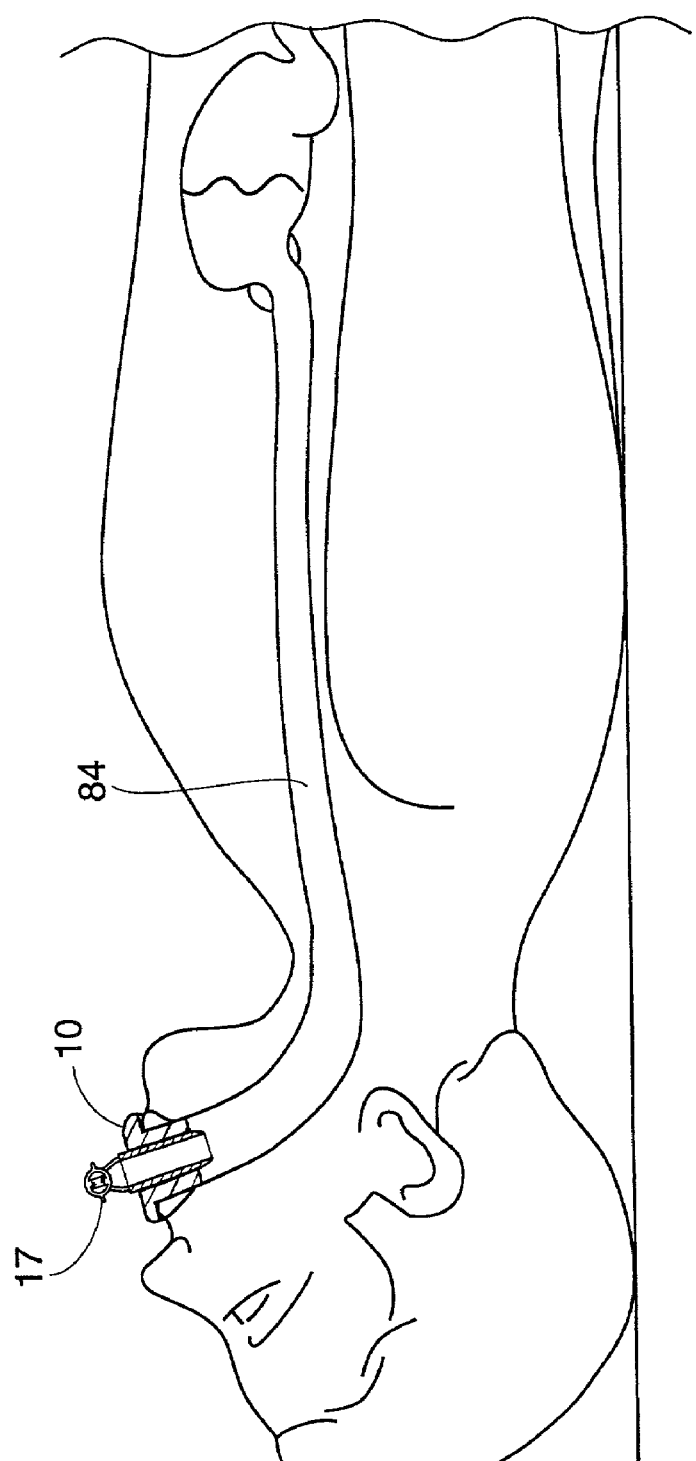
FIG. 17 is a side view of an individual in a reclined position with a bite block carrying a gripping tool inserted in the individuals mouth.

In use, the patient lies awake in a reclined or semi-reclined position. A bite block 10, desirably carrying a gripping tool (T) as previously described (see, e.g., FIG. 1*a*) is placed in the patient's mouth and properly positioned, as illustrated in FIG. 17. The gripping elements 17 are placed in the open (P1) position (as shown in FIG. 3*b*).

Figure 18:
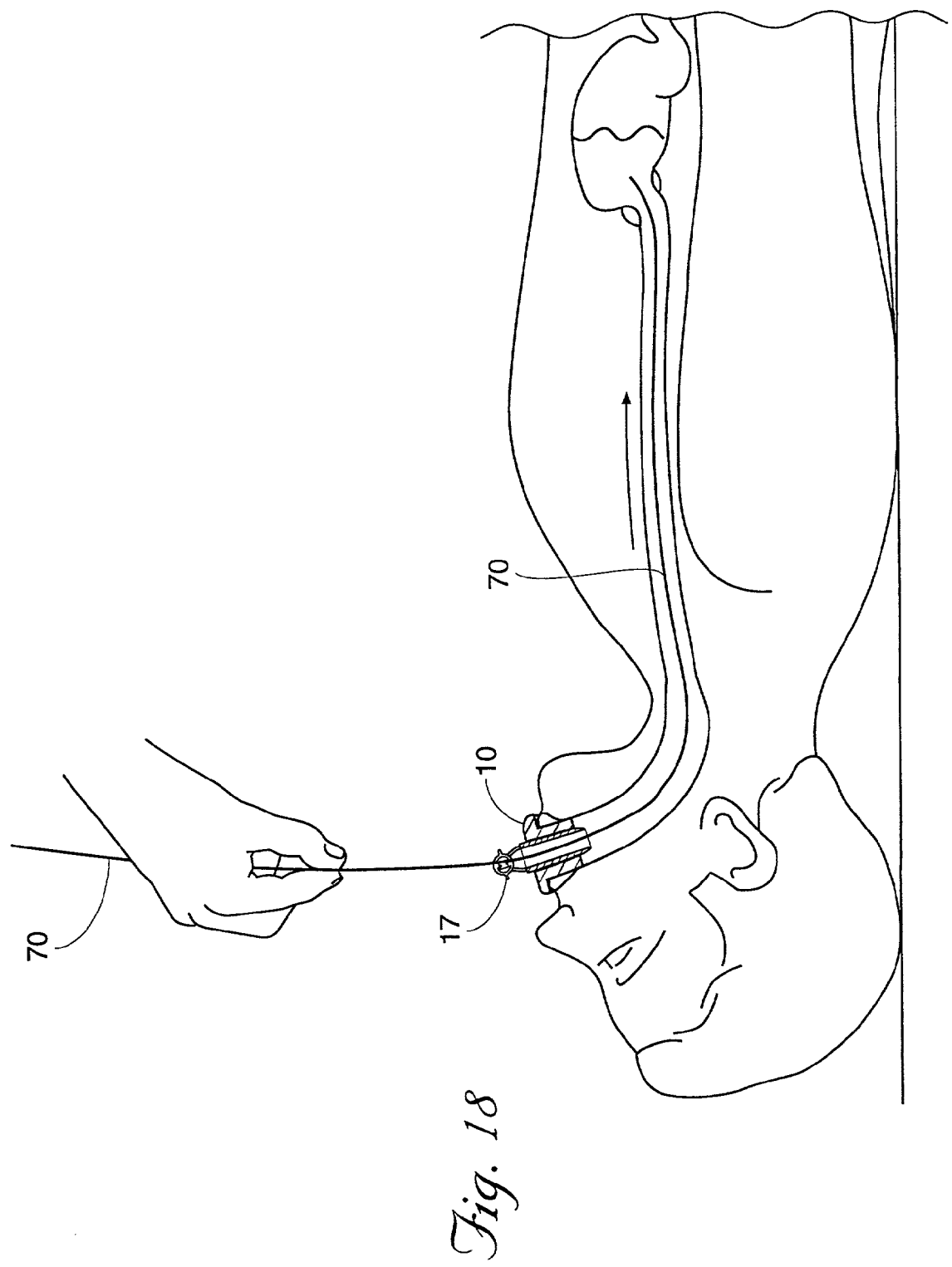
FIG. 18 is a side view of the employment of a guidewire through a bite block carrying a gripping tool and into the esophagus.

The physician passes the small diameter guidewire 70 through the patient's mouth and pharynx, and into the esophagus 84 to the targeted site, as illustrated in FIG. 18.

The targeted site for treatment of GERD is typically the lower esophageal sphincter 90 (see FIG. 21*b*) or the cardia 92 of the stomach (see FIG. 30), or both.

Figure 19:
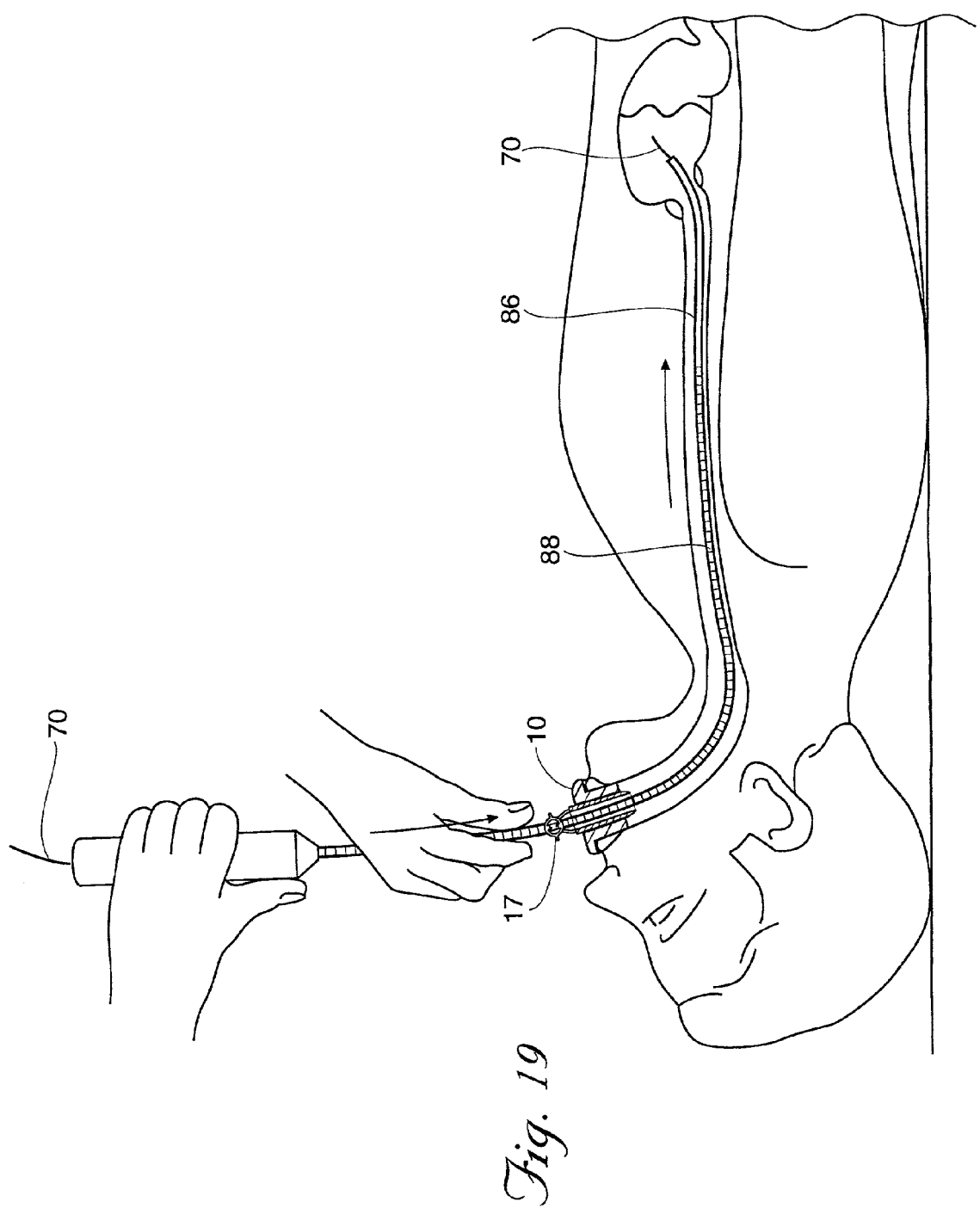
FIG. 19 is a side view of the employment of an endoscope through the bite block carrying a gripping tool and into the esophagus.

The physician preferably employs an endoscope 86 in conjunction with the guidewire 70 for viewing the targeted site. Use of an endoscope 86 is shown in FIG. 19. The endoscope 86 can be either separately employed in a side-by-side relationship with the guidewire 70, or the endoscope 86 may be introduced over the guidewire 70 itself. FIG. 19 illustrates employment of an endoscope 86 over a guidewire 70.

To aid in determining the position of the endoscope 86, the tubal body of the endoscope 86 includes measured markings 88 along its length. The markings 88 indicate the distance between a given location along the tubal body and the endoscope 86.

Relating the alignment of the markings 88 to the bite block 10, the physician can gauge, in either relative or absolute terms, the distance between the patient's mouth and the endoscope 86 in the esophagus 84. When the physician visualizes the desired treatment site, e.g., lower esophageal sphincter 90 (see FIG. 21*b*) or cardia 92 (see FIG. 30), with the endoscope 86, the physician records the markings 88 that align with the bite block 10 and removes the endoscope 86, leaving the guidewire 70 behind.

In the illustrated embodiment, the catheter tube 19 includes measured markings 88 along its length. The measured markings 88 indicate the distance between a given location along the catheter tube 19 and an operative element (e.g., electrodes 60). The markings 88 on the catheter tube 19 correspond in spacing and scale with the measured markings 88 along the tubal body of the endoscope 86.

Figure 20:
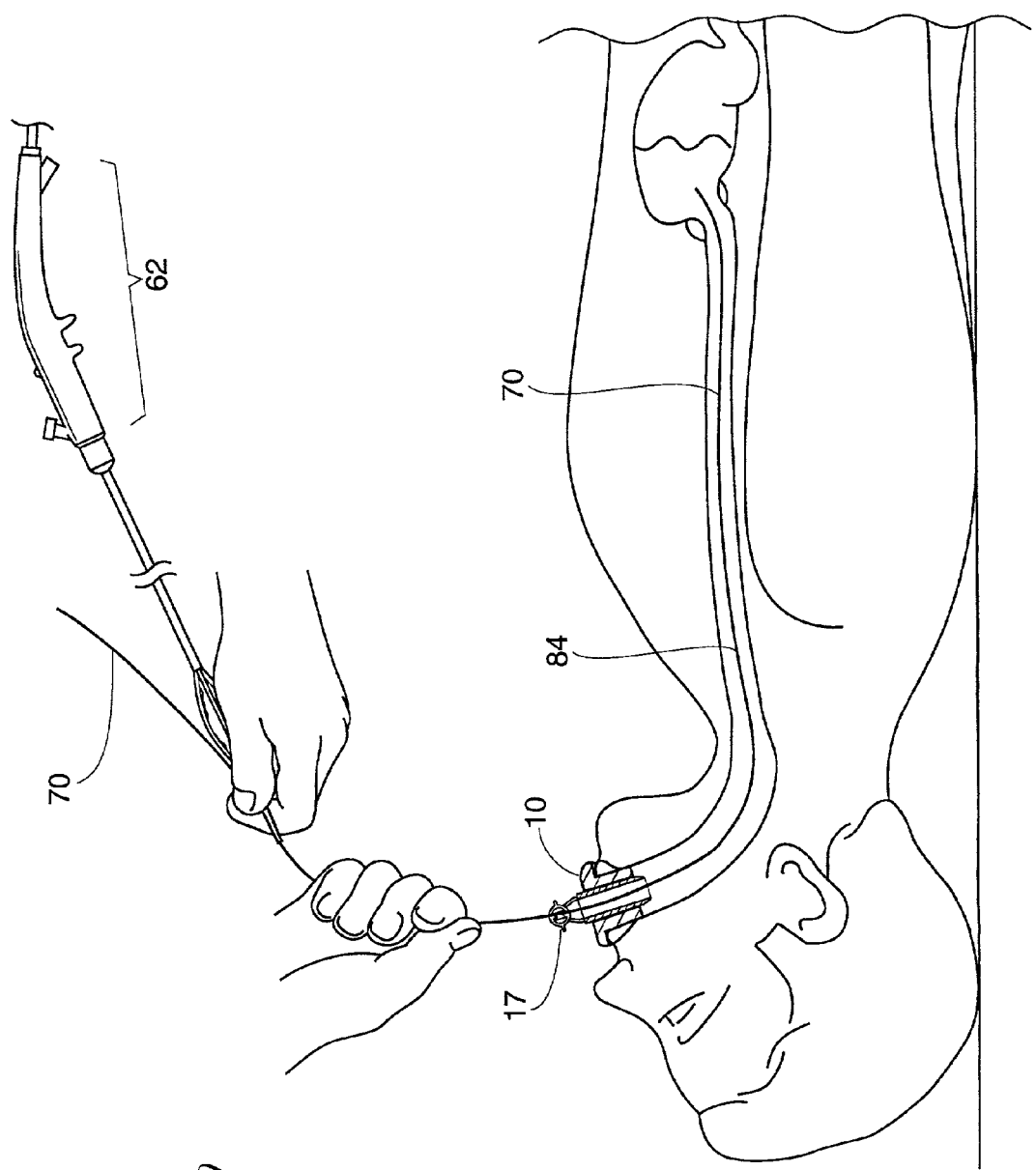
FIG. 20 is a side view illustrating the threading of an employed guidewire through a catheter tip.

The free proximal end of the guidewire 70 is thread through the opening 76 in the distal tail 72 of the expandable structure 64, such that the guidewire 70 exits the distal tail 72 through the orifice 78, as illustrated in FIG. 20.

Figure 21A:
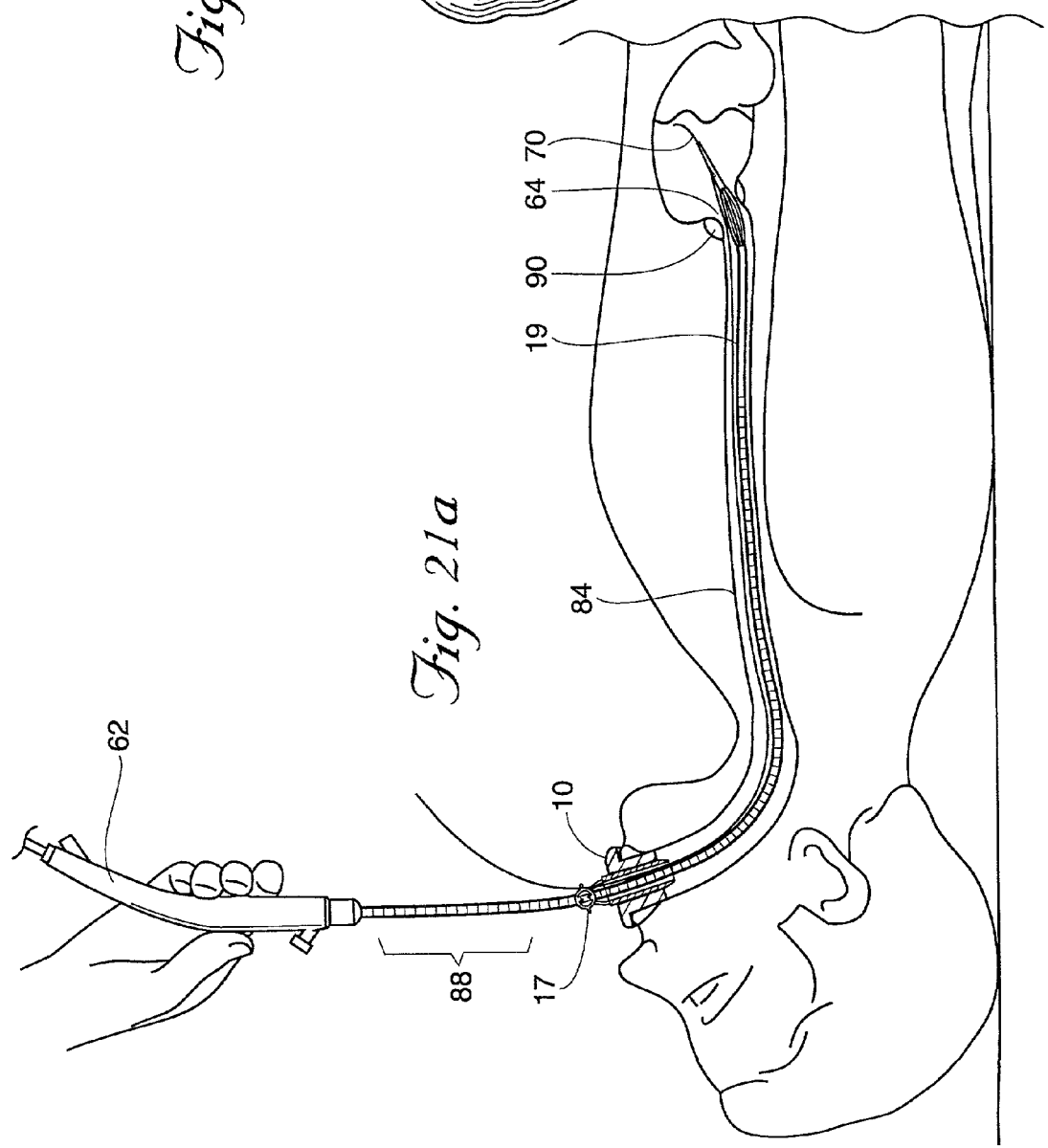
FIG. 21a is a side view illustrating the final positions of the guidewire and the catheter after employment.

The catheter 58 is then advanced along the guidewire 70 through the patient's mouth and pharynx and to the desired position in the esophagus 84, e.g., lower esophageal sphincter 90. The positioning of the catheter 58 in the lower esophageal sphincter 90 is illustrated in FIGS. 21*a* and 21*b*.

Figure 22:
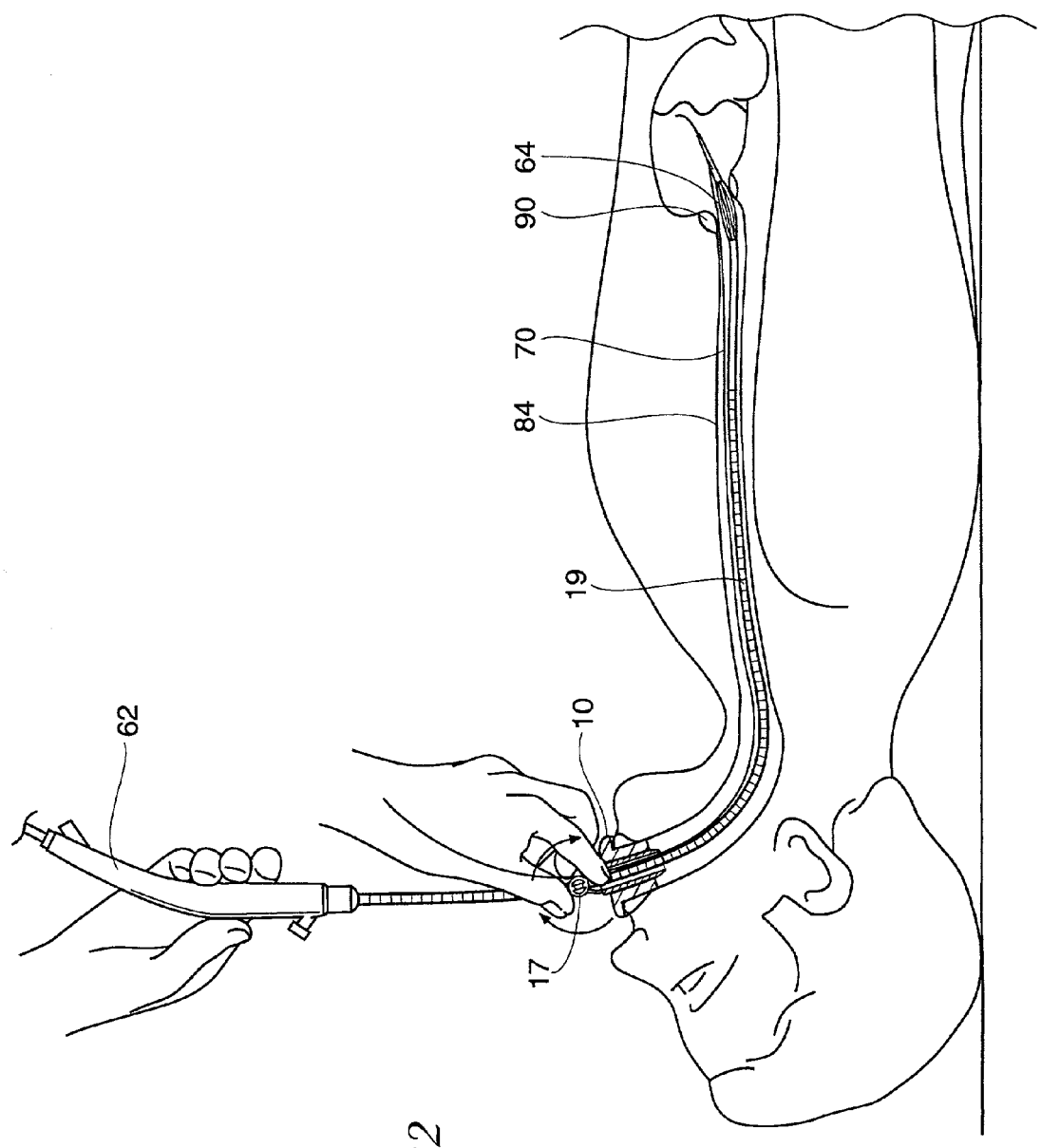
FIG. 22 is a side view of the jaws of the gripping tool being moved to a closed position by manipulation of a cam mechanism.

An ablation sequence is then performed. The sequence typically comprises the following steps. First, the gripping elements 17 of the gripping tool (T) are moved (represented by arrows in FIG. 22) to the closed (P2) position (shown in FIG. 3*a*), thereby holding the catheter 58 fixed in the desired position, as shown in FIG. 22.

Figure 23:
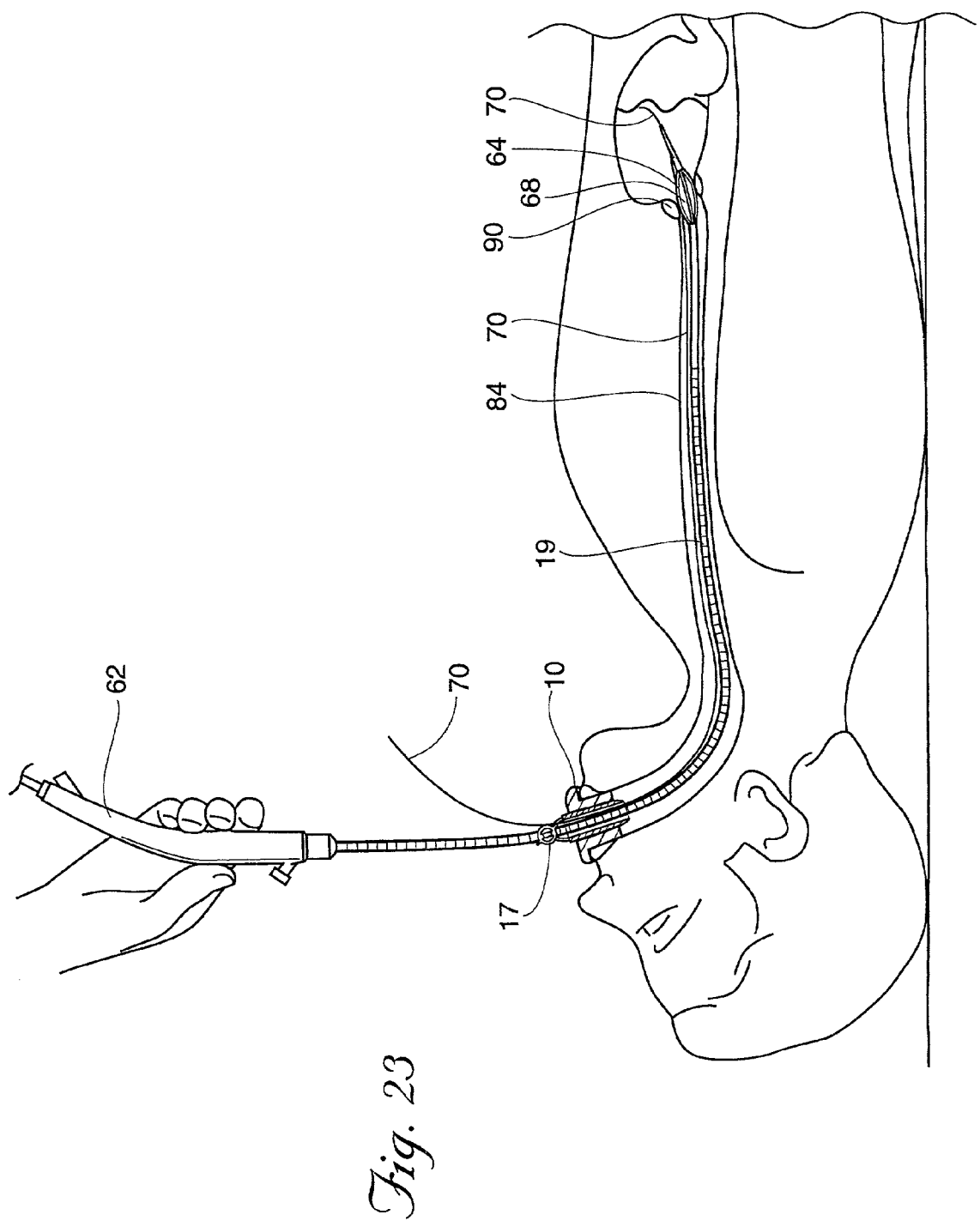
FIG. 23 is a side view illustrating the employed catheter with the expandable structure in an inflated position.

Second, the expandable body 68 is expanded (e.g., sterile water or air is injected into a balloon through a port in the handle 62 of the catheter 58, causing it to inflate). The expandable structure 64 is thereby also expanded. FIG. 23 shows the position of the expandable body 68 after expansion.

Figure 24:
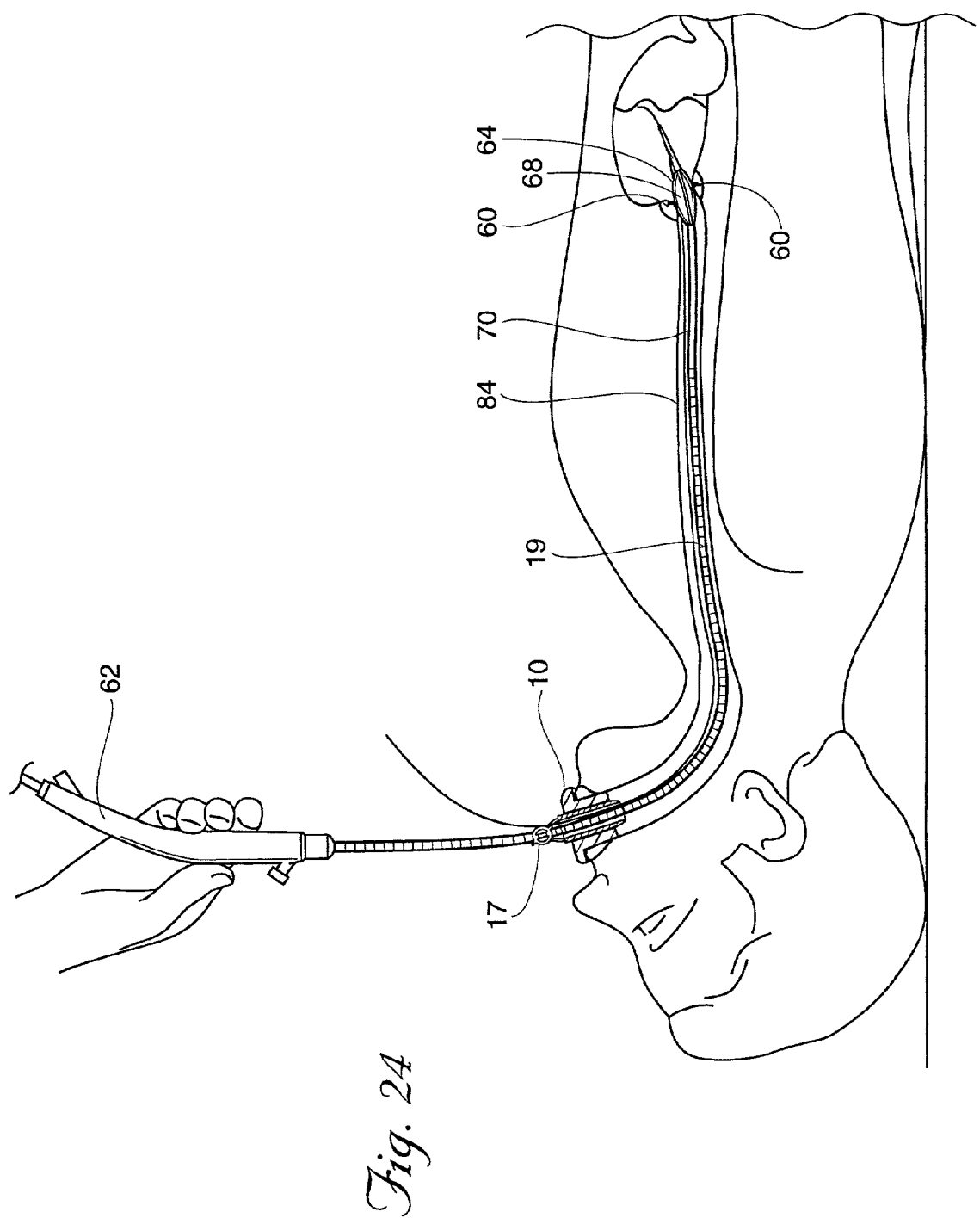
FIG. 24 is a side view illustrating the employed catheter with the expandable structure inflated and the electrodes in an extended position.

Third, the electrodes 60 are extended (e.g., by operation of a push-pull lever on the handle 62 of the catheter 58), as illustrated in FIG. 24.

Fourth, radio frequency energy is applied for a desired period of time (e.g., radio frequency energy in the range of about 400 kHz to about 10 mHz is applied for approximately 90 seconds).

If desired, cooling liquid can be introduced during the ablation sequence (e.g., each spine 66 can include an interior lumen with a port to convey a cooling liquid like sterile water into contact with the mucosal surface of the targeted tissue site) (not shown).

Fifth, the electrodes 60 are retracted (e.g., by operation of a push-pull lever on the handle 62 of the catheter 58).

Sixth, the expandable structure 64 is deflated.

Figure 25:
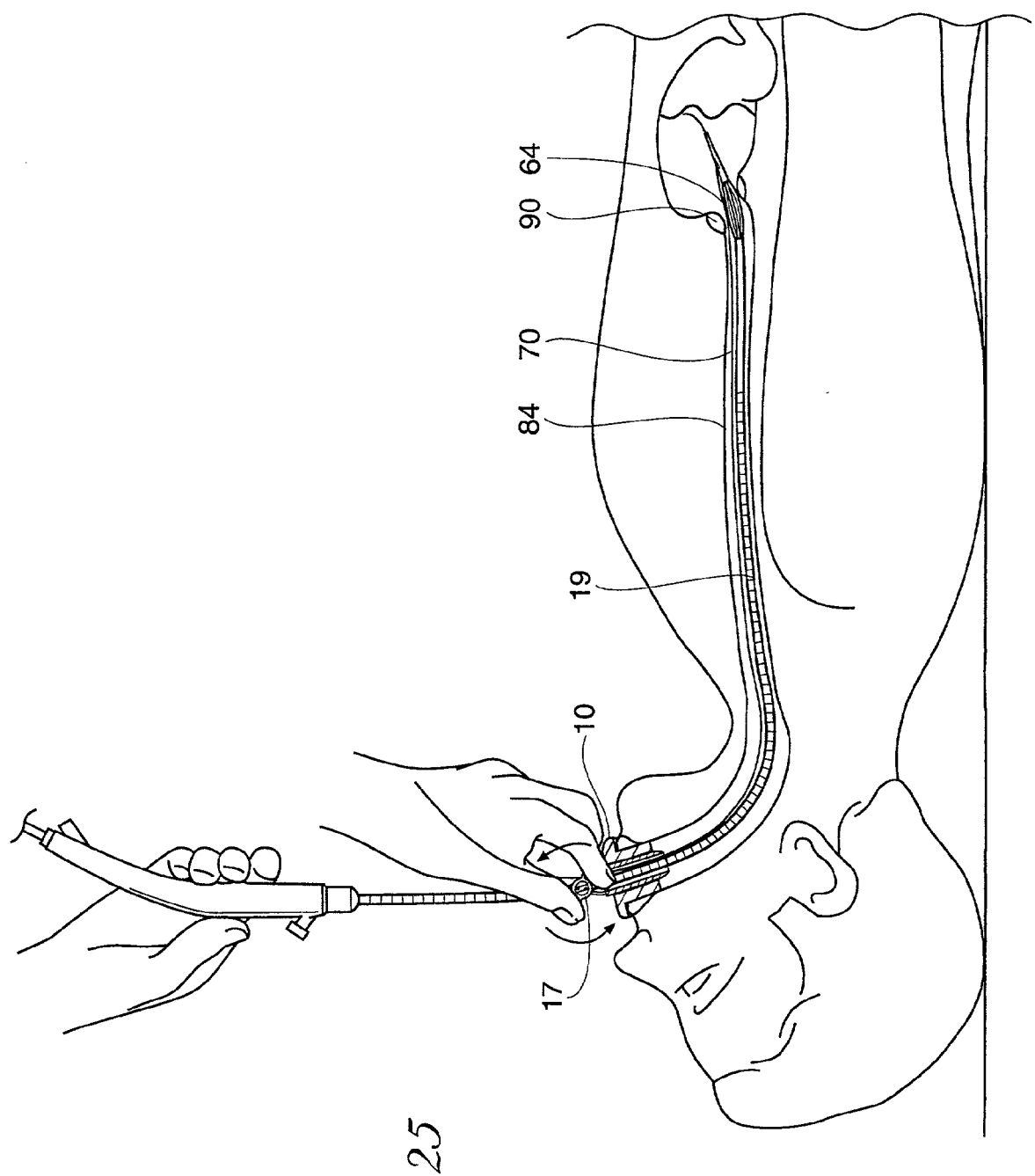
FIG. 25 is a side view of the jaws of the gripping tool being moved to an open position by manipulation of a cam mechanism, with the expandable structure deflated and the electrodes retracted.

Finally, the elements 17 of the gripping tool (T) are moved to the open (P1) position (shown in FIG. 3*b*), thereby enabling the repositioning or removal of the catheter 58. The opening of the elements 17 is illustrated by arrows in FIG. 25.

To create greater lesion density in a given targeted tissue area, it is also desirable to create a pattern of multiple lesions, e.g., in rings along the targeted treatment site.

Figure 30:
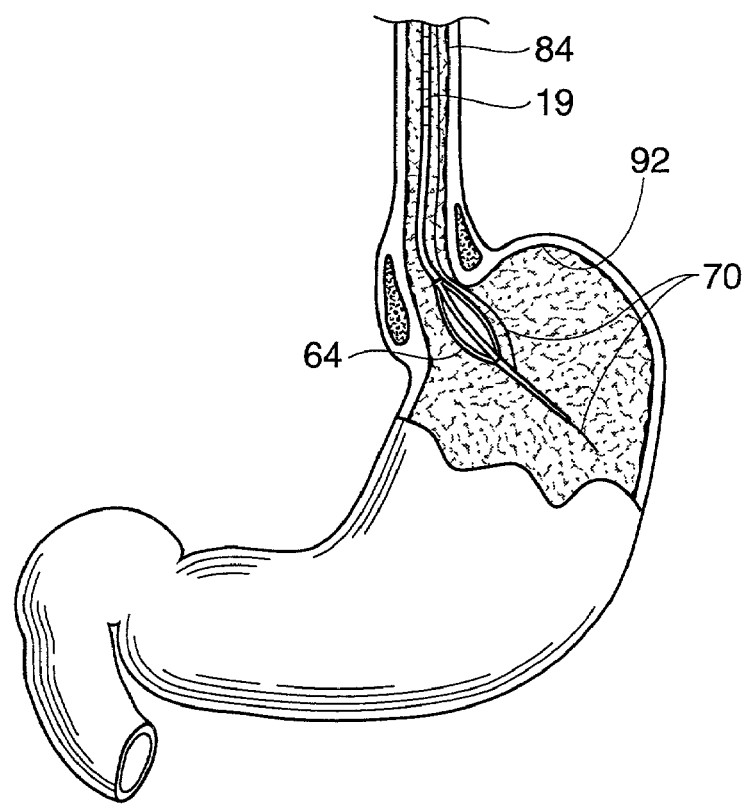
FIG. 30 is a side view showing the positioning of a catheter within the cardia of the stomach.

For example, multiple lesions may be obtained by performing a series of ablation sequences in both the lower esophageal sphincter 90 (see FIG. 21*b*) and the cardia 92 (see FIG. 30). The physician typically performs a series of ablation sequences in the lower esophageal sphincter 90, followed by a series of ablation sequences in the cardia 92, or vice versa.

For example, a "rotational sequence" is first employed in the lower esophageal sphincter 90 (see FIG. 21b). In this sequence, with the elements 17 in the open (P1) position, the catheter 58 is rotated axially a desired number of degrees from the first position, as illustrated by arrows in FIG. 26. The elements 17 of the gripping tool (T) are then moved to the closed (P2) position and a second ablation sequence is performed.

Figure 27A:
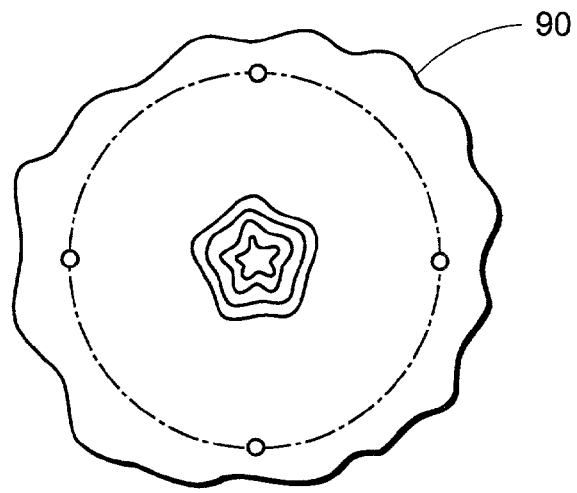
FIG. 27a is a schematic of a lesion pattern after one ablation sequence is completed.
Figure 27B:
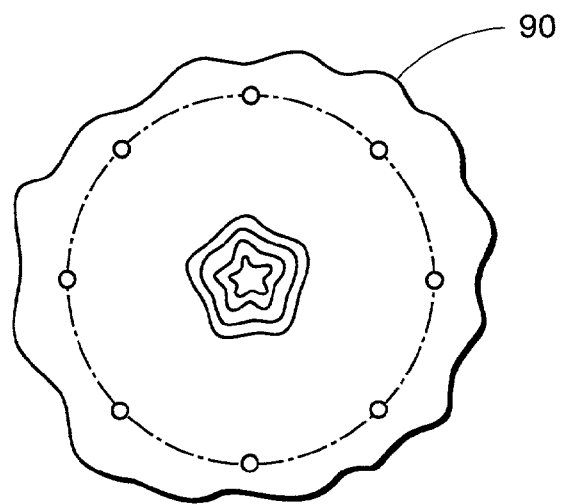
FIG. 27b is a schematic of a lesion pattern after a second ablation sequence is performed following a 45° rotation of the catheter.

The pattern of lesions created by such a rotational sequence is shown in FIGS. 27a–27b. FIG. 27a corresponds to the pattern resulting from the initial ablation sequence. FIG. 27b represents the lesion pattern after one rotation and ablation sequence.

In the illustrated arrangement, the lesion pattern corresponds to four electrodes 60 spaced at 90 degree angles on the catheter 58 (see FIG. 27a). The rotation is of approximately 45 degrees, thereby creating a final lesion pattern comprising a "ring" of eight equidistant lesions (see FIG. 27b).

Of course, a variety of electrode and rotational arrangements may be employed to produce a variety of different lesion patterns.

Figure 28:
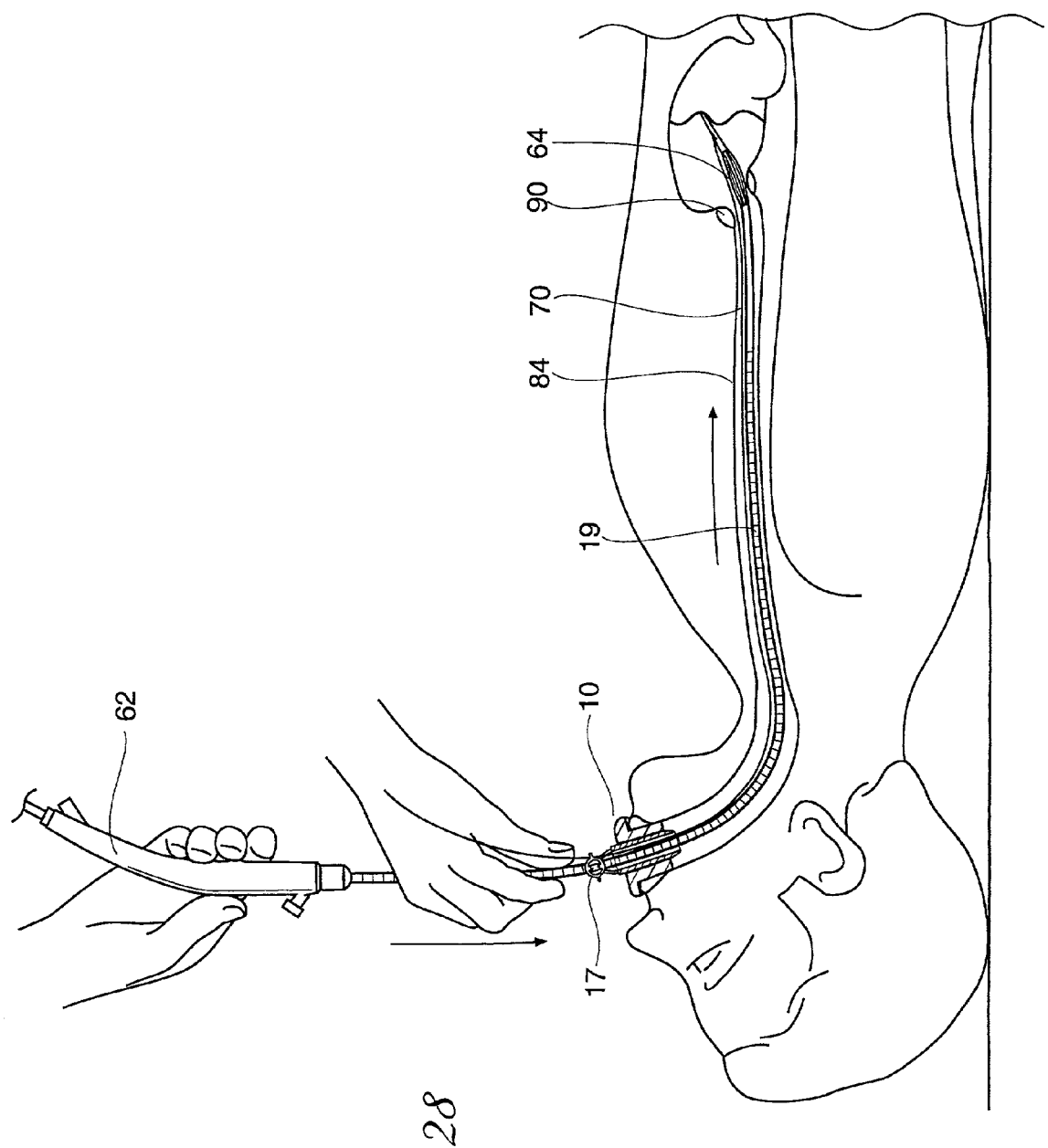
FIG. 28 is a side view of the employed catheter being advanced axially, with the expandable structure deflated and the electrodes retracted.
Figure 29:
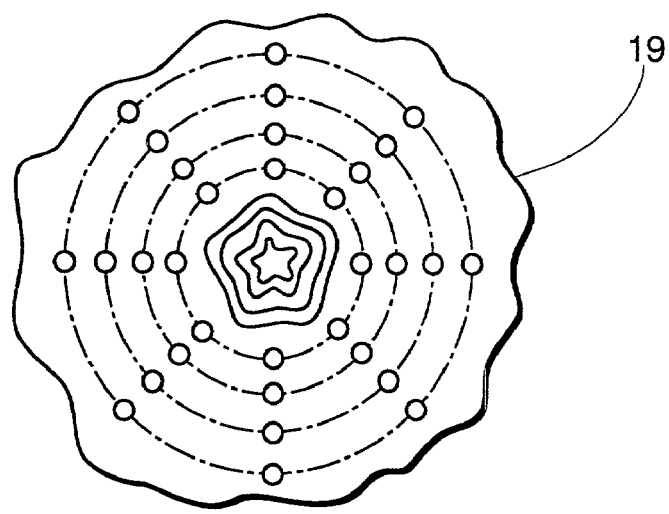
FIG. 29 is a schematic of a lesion pattern after two ablation sequences separated by 45° are performed at each of four levels.

In addition to or in place of a rotational sequence, an "axial sequence" may be employed. This process is illustrated in FIGS. 28–29. In this sequence, with the elements 17 in an open position, the catheter 58 is advanced axially within the lower esophageal sphincter 90 from the site of the first ablation sequence, as illustrated by arrow in FIG. 28.

The elements 17 of the gripping tool (T) are moved to the closed position and a second ablation sequence is then performed. If desired, a rotational sequence is then performed as previously described.

The catheter 58 is then advanced axially from the site of the second ablation sequence and the process is repeated (not shown).

The catheter 58 is then advanced axially from the site of the third ablation sequence and the process is repeated (not shown).

One possible pattern of lesions formed in the lower esophageal sphincter 90 resulting from such a combination of axial and rotational sequences is illustrated in FIG. 29.

FIG. 29 corresponds to the lesion pattern resulting from a rotational ablation sequence being performed at each of four different depths within the lower esophageal sphincter 90. Thus, eight lesions are formed at each of four depths, for a total of thirty-two lesions.

Of course, a variety of rotational and axial arrangements may be employed to produce a variety of different lesion patterns.

It is desirable to also form a lesion pattern in the cardia 92 (see FIG. 30) of the stomach in addition to or in place of the lesion pattern formed in the lower esophageal sphincter 90 (see FIG. 21b).

To this end, after completing the desired lesion pattern in the lower esophageal sphincter 90, the catheter 58 is advanced axially into the cardia 92. The positioning of the catheter within the cardia 92 is illustrated in FIG. 30.

A first ablation sequence is then performed. A rotational sequence is then performed if desired. For example, the catheter is rotated a desired number of degrees and a second ablation sequence is performed. The catheter 58 is then rotated the same number of degrees from the site of the first ablation sequence in the opposite direction and a final ablation sequence is performed.

The pattern of lesions created by such a rotational sequence is shown in FIGS. 31a–31c.

FIG. 31a corresponds to the pattern resulting from the initial ablation sequence. FIG. 31b represents the lesion pattern after the first rotation and ablation sequence. FIG. 31c represents the lesion pattern after the second rotation and ablation sequence.

In the illustrated arrangement, the lesion pattern corresponds to four electrodes 60 spaced at 90 degrees angles on the catheter 58. The rotation is of approximately 22.5 degrees, thereby creating a final lesion pattern of twelve lesions.

It is desirable to create a ring of twelve lesions in the cardia 92 rather than a ring of eight lesions as created in the lower esophageal sphincter 90 to cover the larger surface area of the cardia 92.

This sequence may be repeated at a second depth in the cardia 92. FIG. 32 represents the final lesion pattern created after the sequence is repeated at a second depth. The lesion pattern illustrated is that of twelve lesions created at each two depths, for a total of twenty-four lesions created in the cardia 92.

Of course, a variety of electrode and rotational arrangements may be employed to produce a variety of different lesion patterns.

Upon completion of all desired ablation sequences, the physician assures that the electrodes 60 are retracted and the expandable body 68 is contracted (e.g., air or water is withdrawn from the balloon by a syringe through a port on the handle 62 of the catheter 58) (not shown).

The elements 17 of the gripping tool (T) are then verified as being in the open position, the catheter 58 and guidewire 70 are withdrawn, and the bite block 10 is removed from the patient's mouth (not shown).

III. Alternative Use of Gripping Tool

Any one of the gripping tools (T1–T8) described can also be used with an alternate embodiment of the previously described catheter 58. This alternate embodiment enables the threading of a guidewire 70 outside the body of the catheter 58, through a guidewire lumen 116 within one of the spines 66 of the expandable structure 64.

Figure 33:
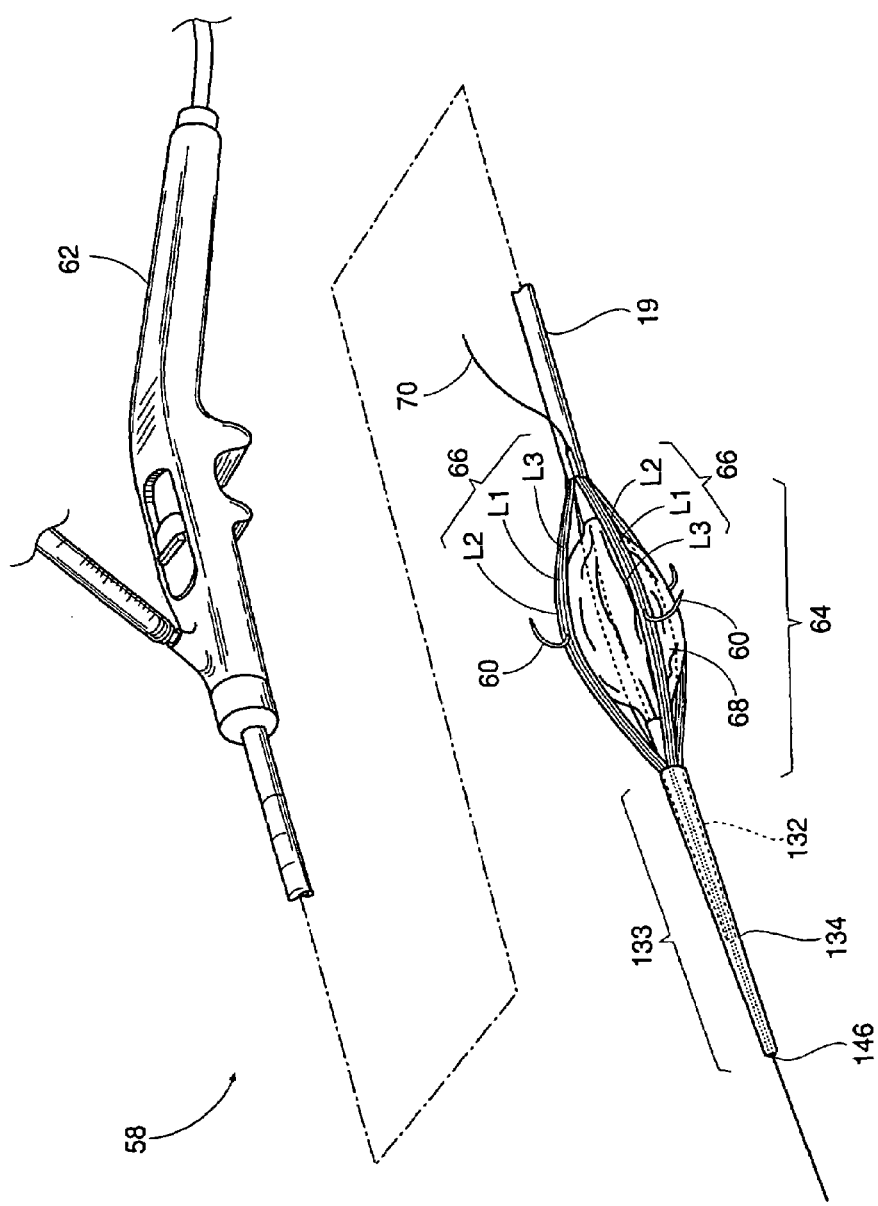
FIG. 33 is a side view of a catheter commonly employed in the treatment of GERD, illustrating an expandable structure comprising an array of tubular spines, one of which accommodates passage of a guidewire.
Figure 34:
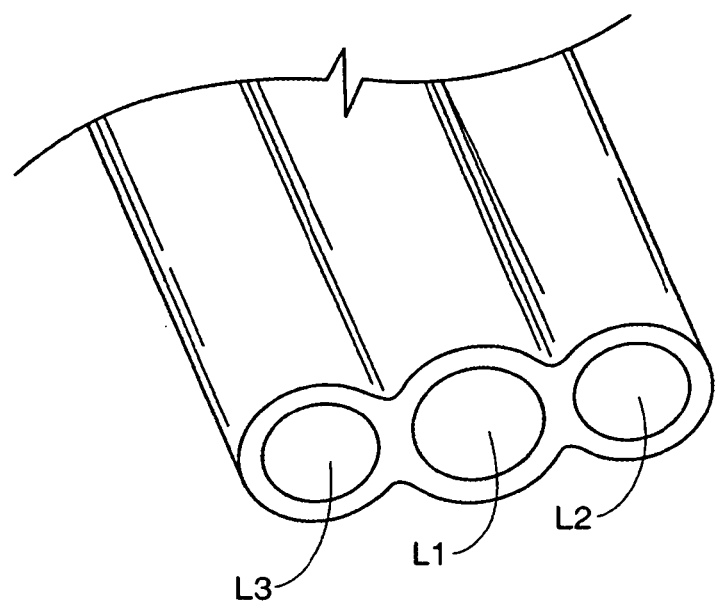
FIG. 34 is a cross-section view of one of the spines of the expandable structure illustrated in FIG. 33, detailing the interior of the three lumens that make up the spine.

As in the previously described embodiment, and as seen in FIG. 33, the expandable structure 64 includes an array of spines 66 that form a basket that is capable of being selectively expanded and contracted. In a representative embodiment, the expandable structure 64 comprises four spines 66. Of course, the expandable structure 64 can include a greater or lesser number of spines 66.

As will be explained in greater detail later, the guidewire lumen 116 passes through one of the spines 66 outside the catheter 58 and outside expandable body 68. The guidewire lumen 116 further extends beyond the distal end of the expandable structure 64 through a distal guide assembly 133.

As FIG. 33 illustrates, each of the spines 66 through which the guidewire 70 does not pass comprises three lumens, designated L1, L2, and L3 in FIG. 33 and subsequent FIGS. 34–40. An arrangement of lumens of this type is detailed in U.S. patent application Ser. No. 09/955,915, filed Sep. 19, 2001, now U.S. Pat. No. 6,699,243, which is herein incorporated by reference.

Figure 35:
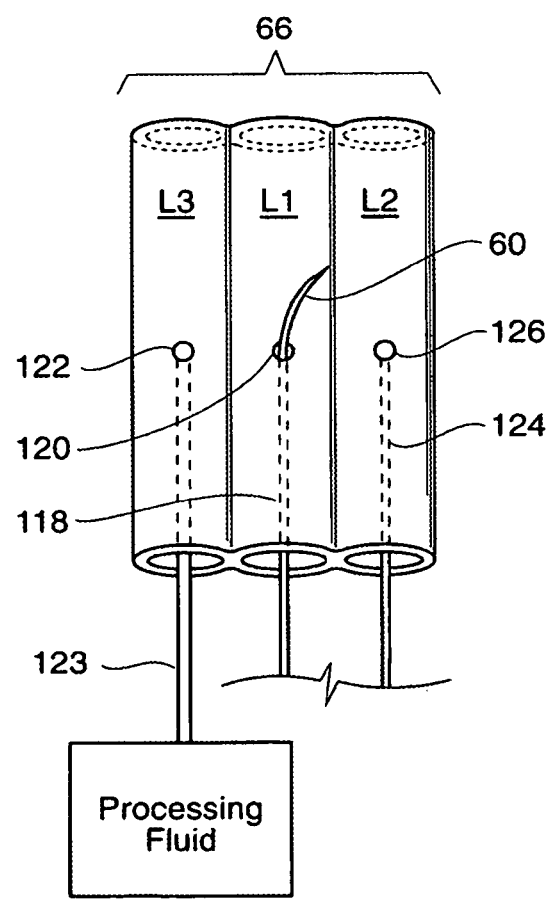
FIG. 35 is a schematic of the exterior surface of a section of the spine shown in FIG. 34, illustrating the positioning of openings within the lumens and electrode and temperature sensing elements carried within the lumens.

As shown in FIG. 35, the first or center passage L1 carries a movable, elongated electrode element 118. The distal end of the electrode element 118 comprises an electrode 60. The electrode element 118 has a retracted position, in which the distal end of the electrode element 118 is contained within the spine 66, and an extended position in which the distal end of the electrode element 118 extends out from the spine 66 and is capable of piercing tissue. FIG. 35 shows the distal end of the electrode element 118 in an extended position. When extended, the electrode 60 exits L1 through an electrode opening 120.

As also shown in FIG. 35, a third passage L3 along side the first passage L1 is coupled to tubing 123 that carries processing fluid from a fluid delivery device. When desired, e.g., to cool tissue during a procedure, fluid is passed through L3 and exits L3 through an irrigation opening 122. The irrigation opening 122 can be generally aligned with the electrode opening 120 so that ablation and cooling occur in the same general tissue region. Alternatively, the irrigation opening 122 can be proximal or distal to the electrode opening 120.

As further shown in FIG. 35, a second passage L2 along side the first passage L1 can carry a temperature sensing element 124, e.g., a thermocouple assembly. In the illustrated embodiment, the thermocouple assembly includes a thermocouple that extends into the L2 lumen and that carries a temperature sensing element 124. The temperature sensing element 124 is exposed through a temperature sensor opening 126. Alternatively, it can extend through the opening 126 and be secured to the spine 66 proximal or distal to the opening 126.

The temperature sensor opening 126 can be generally aligned with the electrode opening 120 and irrigation opening 122 so that ablation, temperature sensing, and cooling occur generally in the same localized tissue region. Alternatively, as above discussed, the openings 120, 122, and 126 can be arranged proximal or distal to each other.

Figure 36A:
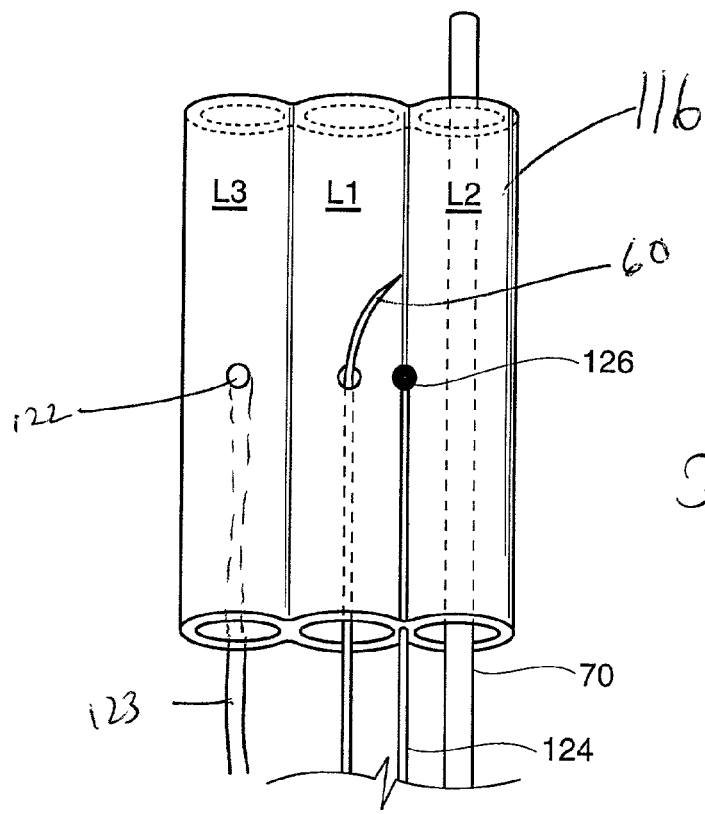
FIG. 36a shows an exterior surface of the spine of the expandable structure illustrated in FIG. 33 that accommodates passage of a guidewire.
Figure 36B:
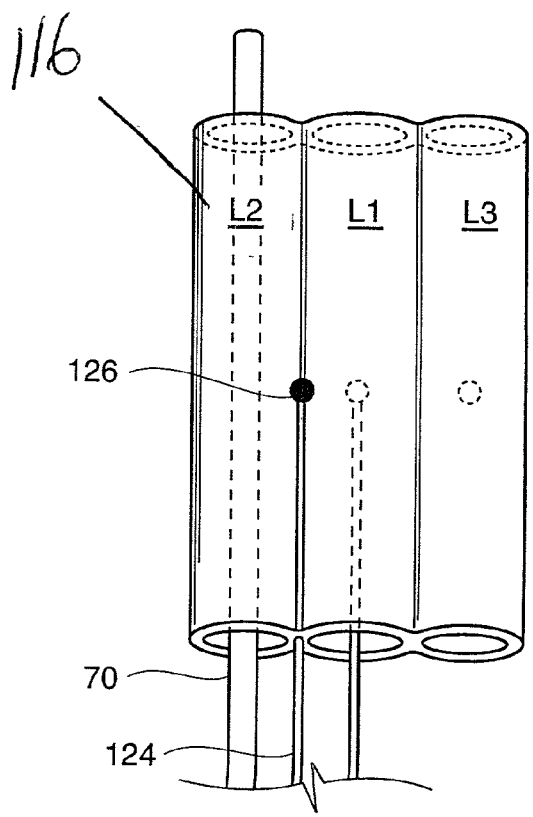

As shown in FIGS. 36a and 36b, the spine 66 that carries the guidewire 70 includes the first and third lumens L1 and L3, which serve to carry, respectively, the electrode 66 and processing fluid tube 123, as previously described. In this arrangement, the lumen L2 is desirably adapted to serve as the guidewire lumen 116 for passage of a guidewire 70, rather than for carrying a temperature sensing element 124.

The guidewire lumen 116 is desirably made of a material that is less stiff than the material of the adjacent L1 and L3 lumens, e.g., polyurethane, polyethelyne, Pebax™, Peek™, or other suitable material. This assures that, with the guidewire 70 inserted, the stiffness of the guidewire lumen 116 will approximate the stiffness of the adjacent L1 and L3 lumens. This assures that the expandable structure 64 is symmetrical upon expansion of the expandable body 68 within the expandable structure 64.

FIG. 36a shows an exterior surface (i.e., the surface of the spine facing away from expandable body 68) of a section of the spine 66 that carries the guidewire lumen 116. FIG. 36b shows an interior surface (i.e., the surface of the spine facing toward the expandable body 68) of the same section of a spine 66.

In this arrangement, as best shown in FIG. 36b, the thermocouple of the temperature sensing element 124 desirably extends along the interior surface of the spine between the L1 and L2 lumens. The temperature sensing element 124 is passed through an opening 126 formed between the two lumens L1 and L2, so that it is exposed on the exterior surface of the spine for use. The temperature sensor opening 126 is desirably aligned with the electrode opening 120 and irrigation opening 122 as previously described.

Figure 40:
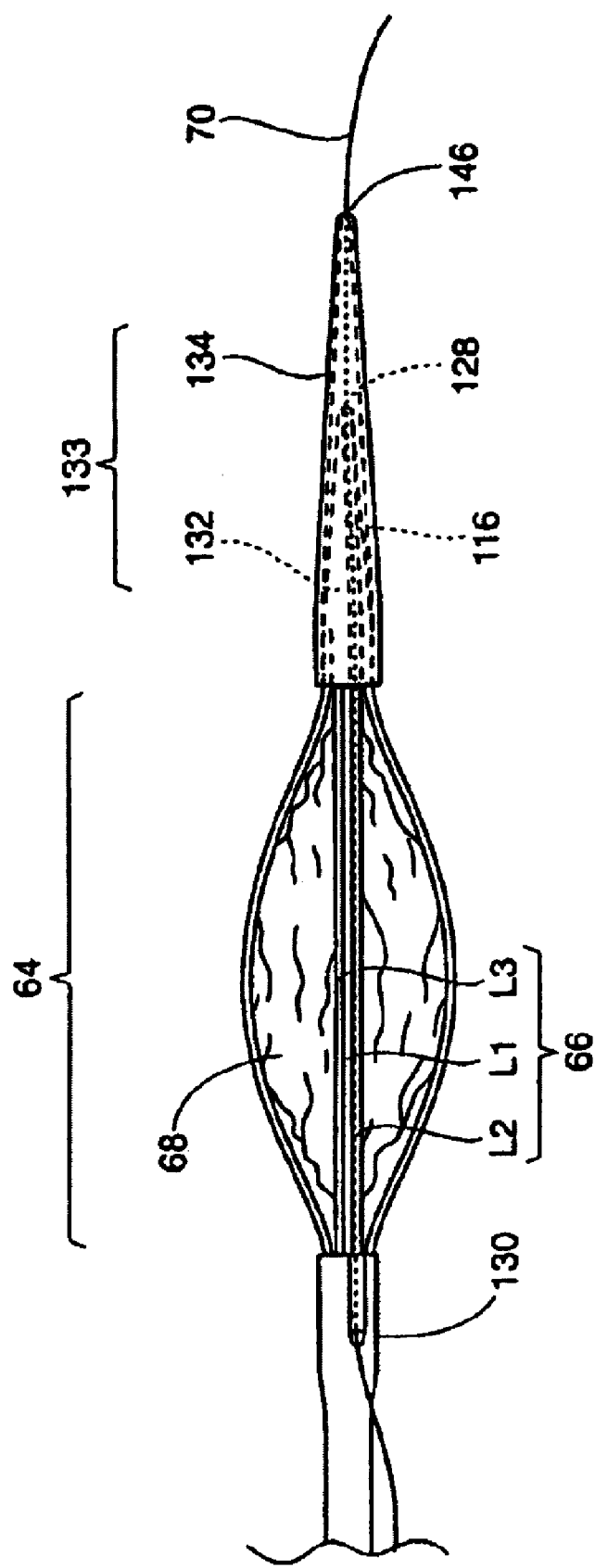
FIG. 40 is a fully assembled side view of the expandable structure shown in FIG. 39, illustrating the placement of the outer and inner sheath of the guide assembly and depicting a guidewire thread through the distal guide assembly and guidewire lumen.

FIG. 40 illustrates a guidewire 70 threaded through the guidewire lumen 116 and the guide assembly 133 (see FIG. 33 also). As illustrated in FIG. 37, the guidewire lumen 116 preferably extends both proximally and distally beyond the adjacent L1 and L3 lumens. The guidewire lumen 116 has a distal opening 128 located beyond the distal end of the expandable structure 64. The opening 128 serves as an exit for a guidewire 70 threaded through the guidewire lumen 116 into the guide assembly 113.

The guidewire lumen 116 also has a proximal opening 130 that extends proximal of the proximal end of the expandable structure 64. As also shown in FIG. 37, the proximal opening 130 rests on the exterior of the catheter tube 19, to provide for an unimpeded passage of the guidewire 70.

The guidewire lumen 116 extends entirely outside the body of the catheter tube 19 and entirely outside the expandable body 68. This path provides stability and support for the expandable structure 64 during passage over the guidewire 70. The passage of the guidewire 70 through the lumen 116 prevents the guidewire 70 from contacting and/or damaging adjacent functional items carried in the expandable structure 64. For example, contact between the guidewire 70 and the energy conducting electrode is prevented, to thereby avoiding conduction of ablation energy by or the heating of the guidewire 70. The passage of the guidewire 70 through the lumen 116 prevents the guidewire 70 from abrading or rupturing the expandable body 68.

As shown in FIG. 37, the distal end of the expandable body 64 includes a guide assembly 133. In the illustrated embodiment, the guide assembly 133 comprises a two piece construction, having an inner sheath 132 and an outer sheath 134.

As shown in FIG. 37, the inner sheath 132 is an elongated member having a proximal region 136 and a distal region 138. In a representative embodiment, the inner sheath 132 is approximately 1.0 inch to 2.5 inches long (in a most preferred embodiment, it is about 1.75 inches long). A groove 140 (see also FIG. 38) formed in the wall of the inner sheath 132 extends in the proximal and distal regions 136 and 138 and serves to receive the guidewire lumen 116.

Figure 39:
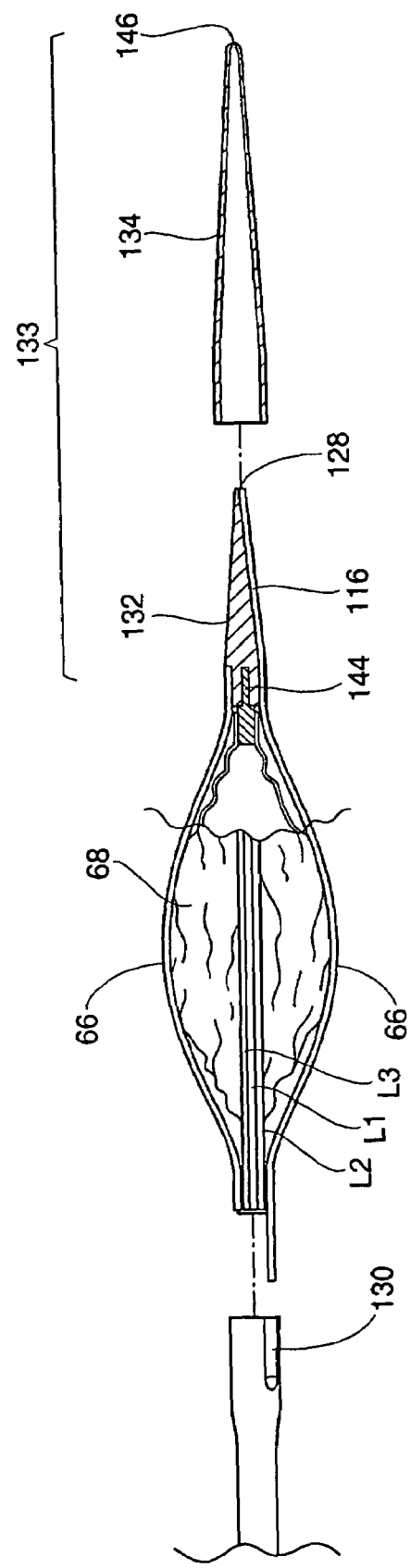
FIG. 39 is a partially assembled side view of the expandable structure shown in FIG. 37, illustrating the attachment of the inner sheath and the coupling of an expandable body to the inner sheath.

As FIG. 37 shows, the distal region 138 is generally round with radially extending vanes 142. In a representative embodiment, the distal region 138 is approximately 1.25 inches long (and the corresponding proximal region 136 being about 0.440 inch long). As illustrated in FIG. 39, the area between the vanes 142 serves to receive the distal end of the spines 66. In the embodiment illustrated in FIG. 38, there are three vanes 142. Of course, a greater or lesser number of vanes 142 may be utilized to accommodate a desired number of spines 66. As shown in FIG. 39, the spines 66 are, e.g., adhesively attached to the inner sheath 132 between the vanes 142.

To aid in stability of the overall assembly and support for the expandable structure 64, the inner sheath 132 is desirably made of a relatively stiff material, having a durometer of, e.g., about 95A.

As seen in FIG. 38, an opening 144 in the proximal region 136 is provided. As illustrated in FIG. 39, the opening 144 serves to couple the distal end of the expandable body 68 to the inner sheath 132.

The distal region 138 of the inner sheath 132 extends in a taper from the proximal region 136. In this arrangement, the distal end of the distal region 138 is approximately even with distal end of the guidewire lumen 116. The guidewire lumen 116, carried by one of the spines 66, is located within the groove 140 and is also, e.g., adhesively attached to the inner sheath 132 along the length of the groove 140.

As FIG. 37 shows, the outer sheath 134 is a hollow, elongated, tapered member adapted, in the illustrated embodiment, to fit over the inner sheath 132. When positioned over the inner sheath 132, the outer sheath 134 extends distally a desired distance beyond the inner sheath 132. In a representative embodiment, the outer sheath 134 is approximately 1.5 inches to 3.5 inches inches long (in a most preferred embodiment, it is about 2.75 inches long). The distal end of the outer sheath 134 includes an opening 146 accommodating passage of a guidewire 70.

The outer sheath 134 is desirably made of a material less stiff than the material selected for the inner sheath 132, e.g., having a durometer of, e.g., about 60A. The reduced stiffness provides minimal discomfort to the patient.

The selection of a relatively stiff material to support the distal end of the expandable structure 64 and of a less stiff material at the distal end of the guide assembly 113 to provide minimal discomfort to the patient, results in a gradient of decreasing stiffness from the proximal end of the guide assembly 113 to the distal end of the guide assembly 113. This maximizes both stability of the assembly and patient comfort.

The inner sheath 132 and outer sheath 134 can be formed by conventional molding techniques. Suitable materials for both the inner and outer sheaths 132 and 134 include Kraton™ and Santoprene™.

Alternately, the inner and outer sheaths 132 and 134 may be molded as a unitary piece utilizing an overmolding process. In this embodiment, the overmolding process permits the manufacture of a single piece having a blended durometer. Thus, a stiffness gradient as previously described can be achieved in a single molded piece.

In use, the patient lies awake in a reclined or semi-reclined position. A bite block 10, desirably carrying a gripping tool (T) as previously described is placed in the patient's mouth and properly positioned (see, e.g., FIG. 17).

In this embodiment, the gripping tool (T) is an embodiment in which the jaw assembly 18 is eccentrically located within the bite block opening 11 (see embodiments T6–T8). The physician passes a small diameter guidewire 70 through the patient's mouth and pharynx, and into the esophagus 84 to the targeted site, as previously described (see FIG. 18). An endoscope can be deployed as previously described (see FIG. 19).

Upon removal of the endoscope, the physician threads the guidewire 70 (see FIGS. 33 and 40) by insertion through the distal opening 146 in the guide assembly 133. The guidewire 70 is advanced into the guidewire lumen 116 of the spine and exits through the proximal opening 130 resting on the exterior surface of the catheter tube 19.

As shown in FIG. 12, the catheter 58 is inserted through the opening 11 in the bite block 10 alongside the jaw assembly 18. The expandable structure 64 is advanced along the guidewire 70 through the patient's mouth and pharynx and to the desired position in the esophagus 84, e.g., lower esophageal sphincter 90. The positioning of the expandable structure 64 in the lower esophageal sphincter 90 is illustrated in FIGS. 21a and 21b.

As seen in FIG. 13, the catheter tube 19 is then moved laterally to position it within the gripping tool (T6, T7, or T8) and the catheter tube 19 is positioned within the gripping tool (T6, T7, or T8), as previously described (see FIGS. 12 and 13).

An ablation sequence as previously described is then performed (see, e.g, FIGS. 27a and 27b). Multiple ablation sequences can be performed to create a desired lesion, as previously described (see e.g., FIG. 29). The jaws of the gripping tool are opened each time the catheter tube 19 is repositioned for a new lesion set. Of course, procedures other than ablation may be performed.

Upon completion of all desired procedures, the physician assures that the electrodes 60 are retracted and the expandable body 68 is contracted (e.g., air or water is withdrawn from the balloon by a syringe through a port on the handle 62 of the catheter 58) (not shown).

The elements 17 of the gripping tool (T) are then verified as being in the open position, the catheter 58 and guidewire 70 are withdrawn, and the bite block 10 is removed from the patient's mouth.

While the embodiment just described details the use of the guidewire lumen 116 located within the tubular spines 66 in combination with a gripping tool (T) having an eccentric jaw assembly 18 (see embodiments T6–T8), it is to be understood that this embodiment of the guidewire lumen 116 is also adapted for use with a gripping tool (T) having a centrally located jaw assembly 18 (see embodiments T1–T5).

Features and advantages of the invention are set forth in the following claims.

We claim:

1. An assembly for treating a tissue region comprising a catheter tube having a distal end,
an expandable structure comprising first and second spines arranged in a desired circumferential array to define a basket assembly projecting beyond the distal end of the catheter tube and including a far end, and
a distal tip assembly having a proximal region and a distal region and projecting beyond the far end of the basket assembly, the distal tip assembly including a rigid first member adapted to engage at least one of the first and second spines to maintain the first and second spines in the desired circumferential array, and a less rigid second member, the second member being sized and configured to overlap the first member, at least in part, to couple the first and second members, whereby the second member extends beyond the first member to provide a gradient of decreasing stiffness from the proximal region to the distal region.

2. An assembly according to claim 1 wherein at least one of the first and second spines carries an electrode.

3. An assembly according to claim 1, further comprising an inflatable member positioned in an interior of the basket assembly, the inflatable member having an inflated condition that expands the basket assembly.

4. An assembly according to claim 1 wherein the first member accommodates passage of a guidewire.

5. An assembly according to claim 1 wherein the second member accommodates passage of a guidewire.

6. An assembly according to claim 5 wherein the second member accommodates passage of a guidewire without threading the guidewire through the catheter tube.

7. An assembly according to claim 1 wherein the first member includes a first guidewire lumen, wherein the second member includes a second guidewire lumen, and
wherein the first guidewire lumen communicates with the second guidewire lumen to permit passage of a guidewire through the first and second members.

8. An assembly according to claim 1 wherein the second member is sized and configured to be removably coupled to the first member.

* * * * *